(12) United States Patent
Hu et al.

(10) Patent No.: US 11,341,649 B2
(45) Date of Patent: May 24, 2022

(54) SYSTEMS AND METHODS FOR QUANTIFYING MULTISCALE COMPETITIVE LANDSCAPES OF CLONAL DIVERSITY IN GLIOBLASTOMA

(71) Applicants: Mayo Foundation for Medical Education and Research, Rochester, MN (US); Arizona Board of Regents on Behalf of Arizona State University, Scottsdale, AZ (US)

(72) Inventors: Leland S. Hu, Phoenix, AZ (US); Kristin R. Swanson, Phoenix, AZ (US); J. Ross Mitchell, Scottsdale, AZ (US); Nhan L. Tran, Peoria, AZ (US); Jing Li, Tempe, AZ (US); Teresa Wu, Gilbert, AZ (US)

(73) Assignees: Mayo Foundation for Medical Education and Research, Rochester, ME (US); Arizona Board of Regents, Scottsdale, AZ (US)

( * ) Notice: Subject to any disclaimer, the term of this patent is extended or adjusted under 35 U.S.C. 154(b) by 3 days.

(21) Appl. No.: 16/975,647

(22) PCT Filed: Feb. 26, 2019

(86) PCT No.: PCT/US2019/019687
§ 371 (c)(1),
(2) Date: Aug. 25, 2020

(87) PCT Pub. No.: WO2019/165475
PCT Pub. Date: Aug. 29, 2019

(65) Prior Publication Data
US 2020/0410683 A1     Dec. 31, 2020

Related U.S. Application Data

(60) Provisional application No. 62/635,276, filed on Feb. 26, 2018.

(51) Int. Cl.
*G06K 9/00*     (2022.01)
*G06T 7/00*     (2017.01)
*G06T 7/11*     (2017.01)

(52) U.S. Cl.
CPC .............. *G06T 7/0016* (2013.01); *G06T 7/11* (2017.01); *G06T 2207/10088* (2013.01);
(Continued)

(58) Field of Classification Search
CPC ..................... G06T 7/0016; G06T 7/11; G06T 2207/10088; G06T 2207/20081;
(Continued)

(56) References Cited

U.S. PATENT DOCUMENTS

2013/0039548 A1   2/2013  Nielsen
2016/0196648 A1   7/2016  Madabhushi
(Continued)

FOREIGN PATENT DOCUMENTS

WO   2019100032   5/2019
WO   2019165475   8/2019

OTHER PUBLICATIONS

Unknown. "Quantifying Multiscale Competitive Landscapes of Clonal Diversity in Glioblastoma"; NCI Funded Cancer Systems Biology Consortium U01; Publication [online]. May 14, 2017 [retrieved Apr. 24, 2019], Retrieved from the Internet: URL:http://mathematicalneurooncology.ort/?page_id=68; pp. 1-3.
(Continued)

*Primary Examiner* — Atiba O Fitzpatrick
(74) *Attorney, Agent, or Firm* — Quarles & Brady LLP

(57) ABSTRACT

Methods that implement image-guided tissue analysis, MRI-based computational modeling, and imaging informatics to analyze the diversity and dynamics of molecularly-distinct subpopulations and the evolving competitive landscapes in human glioblastoma multiforme ("GBM") are provided.
(Continued)

Machine learning models are constructed based on multi-parametric MRI data and molecular data (e.g., CNV, exome, gene expression). Models can also be built based on specific biological factors, such as sex and age. Inputting MRI data into the trained predictive models generates maps that depict spatial patterns of molecular markers, which can be used to quantify and co-localize regions molecularly distinct subpopulations in tumors and other regions, such as the non-enhancing parenchyma, or brain around tumor ("BAT") regions.

21 Claims, 9 Drawing Sheets

(52) U.S. Cl.
CPC ............... *G06T 2207/20081* (2013.01); *G06T 2207/20084* (2013.01); *G06T 2207/30016* (2013.01); *G06T 2207/30096* (2013.01)

(58) Field of Classification Search
CPC . G06T 2207/20084; G06T 2207/30016; G06T 2207/30096
See application file for complete search history.

(56) References Cited

U.S. PATENT DOCUMENTS

| | | | | |
|---|---|---|---|---|
| 2017/0071496 | A1* | 3/2017 | Gillies | A61B 5/0263 |
| 2017/0103525 | A1 | 4/2017 | Hu | |
| 2017/0309025 | A1 | 10/2017 | O'Rourke et al. | |
| 2018/0342058 | A1 | 11/2018 | Madabhushi et al. | |
| 2020/0027557 | A1* | 1/2020 | Karow | G16H 50/30 |
| 2020/0081085 | A1 | 3/2020 | Tiwari | |
| 2021/0398286 | A1* | 12/2021 | O'Rourke | G06T 7/0012 |

OTHER PUBLICATIONS

Weber, M.-A. et al. Biopsy targeting gliomas: do functional imaging techniques identify similar target areas? Invest. Radiol. 45, 755-768 (2010).
Woolrich, M. W. et al. Bayesian analysis of neuroimaging data in FSL. Neuroimage 45, S173-86 (2009).
Yang, D., et al. Evaluation of tumor-derived MRI-texture features for discrimination of molecular subtypes and prediction of 12-month survival status in glioblastoma. Med. Phys. 42, 6725-6735 (2015).
Zhou, M. et al. Radiologically Defined Ecological Dynamics and Clinical Outcomes in Glioblastoma Multiforme Preliminary Results. Transl. Oncol. 7, 5-13 (2014).
Aghi, M. et al. Magnetic resonance imaging characteristics predict epidermal growth factor receptor amplification status in glioblastoma. Clin. Cancer Res. 11, 8600-8605 (2005).
Andor, N. et al. Pan-cancer analysis of the extent and consequences of intratumor heterogeneity. Nat. Med. 22, 105-113(2015).
Baldock, A. L. et al. From patient-specific mathematical neuro-oncology to precision medicine. Front. Oncol. 3, 62 (2013).
Barajas, R. F., Jr et al. Glioblastoma Multiforme Regional Genetic and Cellular Expression Patterns: Influence on Anatomic and Physiologic MR Imaging 1. Radiology 254, 564-576 (2010).
Brown, R. et al. The use of magnetic resonance imaging to noninvasively detect genetic signatures in oligodendroglioma. Clin. Cancer Res. 14, 2357-2362 (2008).
Christoforides, A. et al. Identification of somatic mutations in cancer through Bayesian-based analysis of sequenced genome pairs. BMC Genomics 14, 302 (2013).
Cibulskis, K. et al. Sensitive detection of somatic point mutations in impure and heterogeneous cancer samples. Nat. Biotechnol. 31, 213-219 (2013).

Dang, M. et al. MRI texture analysis predicts p53 status in head and neck squamous cell carcinoma. AJNR Am. J. Neuroradiol. 36, 166-170 (2015).
Dezso, Z. et al. Identifying disease-specific genes based on their topological significance in protein networks. BMC Syst. Biol. 3, 36 (2009).
Drabycz, S. et al. An analysis of image texture, tumor location, and MGMT promoter methylation in glioblastoma using magnetic resonance imaging. Neuroimage 49, 1398-1405 (2010).
Drabycz, S., et al. Image texture characterization using the discrete orthonormal S-transform. J. Digit. Imaging 22, 696-708 (2009).
Ellingson, B. M. et al. Validation of functional diffusion maps (fDMs) as a biomarker for human glioma cellularity. J. Magn. Reson. Imaging 31, 538-548 (2010).
Fedorov, A. et al. 3D Slicer as an image computing platform for the Quantitative Imaging Network. Magn. Reson. Imaging 30, 1323-1341 (2012).
Galban, C. J. et al. Prospective analysis of parametric response map-derived MRI biomarkers: identification of early and distinct glioma response patterns not predicted by standard radiographic assessment. Clin. Cancer Res. 17, 4751-4760 (2011).
Giannini, C. Patient tumor EGFR and PDGFRA gene amplifications retained in an invasive intracranial xenograft model of glioblastoma multiforme. Neuro. Oncol. 7, 164-176 (2005).
Gupta, A. et al. Pretreatment Dynamic Susceptibility Contrast MRI Perfusion in Glioblastoma: Prediction of EGFR Gene Amplification. Clin. Neuroradiol. 25, 143-150 (2015).
Gutman, D. A. et al. MR imaging predictors of molecular profile and survival: multi-institutional study of the TCGA glioblastoma data set. Radiology 267, 560-569 (2013).
Haralick, R. M., et al. Textural features for image classification. Systems, Man and Cybernetics, IEEE Transactions on 610-621 (1973).
Harpold, H. L. P., et al. The evolution of mathematical modeling of glioma proliferation and invasion. J. Neuropathol. Exp. Neurol. 66, 1-9 (2007).
Hartung, N. et al. Mathematical modeling of tumor growth and metastatic spreading: validation in tumor-bearing mice. Cancer Res. 74, 6397-6407 (2014).
Hartung, N. Modelling of metastatic growth and in vivo imaging. (Aix-Marseille, 2014).
Hawkins-Daarud, A., et al. Modeling Tumor-Associated Edema in Gliomas during Anti-Angiogenic Therapy and Its Impact on Image-able Tumor. Front. Oncol. 3, 66 (2013).
Hu, L. et al., in "Reevaluating the Imaging Definition of Tumor Progression: Perfusion MRI Quantifies Recurrent Glioblastoma Tumor Fraction, Pseudoprogression, and Radiation Necrosis to Predict Survival," Neuro. Oncol., 2012 14:919-930.
Hu, L. S. et al. "Radiogenomics to characterize regional genetic heterogeneity in glioblastoma." Neuro-oncology 19.1 (2017): 128-137.
Hu, L. S. et al. Correlations between perfusion MR imaging cerebral blood vol. microvessel quantification, and clinical outcome using stereotactic analysis in recurrent high-grade glioma. AJNR Am. J. Neuroradiol. 33, 69-76 (2012).
Hu, L. S. et al. Multi-Parametric MRI and Texture Analysis to Visualize Spatial Histologic Heterogeneity and Tumor Extent in Glioblastoma. PLoS One 10, e0141506 (2015).
Hu, L. S. et al. Relative cerebral blood volume values to differentiate high-grade glioma recurrence from posttreatment radiation effect: direct correlation between image-guided tissue histopathology and localized dynamic susceptibility-weighted contrast-enhanced perfusion MR imaging measurements. AJNR Am. J. Neuroradiol. 30, 552-558 (2009).
International Searching Authority. International Search Report and Written Opinion for application PCT/US2019/019687, dated May 7, 2019.
Itakura, H. et al. Magnetic resonance image features identify glioblastoma phenotypic subtypes with distinct molecular pathway activities. Sci. Transl. Med. 7, 303ra138 (2015).

(56) References Cited

OTHER PUBLICATIONS

Jain, R. et al. Outcome prediction in patients with glioblastoma by using imaging, clinical, and genomic biomarkers focus on the nonenhancing component of the tumor. Radiology 272, 484-493 (2014).

Kalpathy-Cramer, J., et al. Advanced magnetic resonance imaging of the physical processes in human glioblastoma. Cancer Res. 74, 4622-4637 (2014).

Laviolette, P. S. et al. Precise ex vivo histological validation of heightened cellularity and diffusion-restricted necrosis in regions of dark apparent diffusion coefficient in 7 cases of high-grade glioma. Neuro. Oncol. 16, 1599-1606 (2014).

Marusyk, A., et al. Intra-tumour heterogeneity: a looking glass for cancer? Nat. Rev. Cancer 12, 323-334 (2012).

Massey, S. C., et al. Glial progenitor cell recruitment drives aggressive glioma growth: mathematical and experimental modelling. J. R. Soc. Interface 9, 1757-1766 (2012).

Neal, M. L. et al. Response classification based on a minimal model of glioblastoma growth is prognostic for clinical outcomes and distinguishes progression from pseudoprogression. Cancer Res. 73, 2976-2986 (2013).

Price, S. J. et al. Improved delineation of glioma margins and regions of infiltration with the use of diffusion tensor imaging: an image-guided biopsy study. AJNR Am. J. Neuroradiol. 27, 1969-1974 (2006).

Price, S. J. The role of advanced MR imaging in understanding brain tumour pathology. Br. J. Neurosurg. 21, 562-575 (2007).

Ramkumar, S. et al. Multiparametric Magnetic Resonance Imaging and Texture Analysis to Distinguish Sinonasal Inverted Papilloma from Squamous Cell Carcinoma. J. Neurol. Surg. B Skull Base 77, A041 (2016).

Rockne, R. et al. Predicting the efficacy of radiotherapy in individual glioblastoma patients in vivo: a mathematical modeling approach. Phys. Med. Biol. 55, 3271-3285 (2010).

Rockne, R., et al. A mathematical model for brain tumor response to radiation therapy. J. Math. Biol. 58, 561-578 (2009).

Ryoo, I. et al. Cerebral blood volume calculated by dynamic susceptibility contrast-enhanced perfusion MR imaging preliminary correlation study with glioblastoma genetic profiles. PLoS One 8, e71704 (2013).

Semmineh, N. B. et al. Assessing tumor cytoarchitecture using multiecho DSC-MRI derived measures of the transverse relaxivity at tracer equilibrium (TRATE). Magn. Reson. Med. 74, 772-784 (2015).

Sottoriva, A. et al. Intratumor heterogeneity in human glioblastoma reflects cancer evolutionary dynamics. Proc. Natl. Acad. Sci. U. S. A. 110, 4009-4014 (2013).

Stadlbauer, A. et al. Gliomas: histopathologic evaluation of changes in directionality and magnitude of water diffusion at diffusion-tensor MR imaging. Radiology 240, 803-810 (2006).

Swanson, K. R. et al. A mathematical modelling tool for predicting survival of individual patients following resection of glioblastoma: a proof of principle. Br. J. Cancer 98, 113-119 (2008).

Swanson, K. R. et al. A quantitative model for differential motility of gliomas in grey and white matter. Cell Prolif. 33, 317-329 (2000).

Swanson, K. R. et al. A quantitative model for the dynamics of serum prostate-specific antigen as a marker for cancerous growth: an explanation for a medical anomaly. Am. J. Pathol. 158, 2195-2199 (2001).

Swanson, K. R. et al. Quantifying efficacy of chemotherapy of brain tumors with homogeneous and heterogeneous drug delivery. Acta Biotheor. 50, 223-237 (2002).

Swanson, K. R. Mathematical modeling of the growth and control of tumors. (1999). In two parts due to file size.

Tykocinski, E. S. et al. Use of magnetic perfusion-weighted imaging to determine epidermal growth factor receptor variant III expression in glioblastoma. Neuro. Oncol. 14, 613-623 (2012).

\* cited by examiner

SYSTEMS AND METHODS FOR QUANTIFYING MULTISCALE COMPETITIVE LANDSCAPES OF CLONAL DIVERSITY IN GLIOBLASTOMA

CROSS-REFERENCE TO RELATED APPLICATIONS

This application is a 371 U.S. National Phase application of PCT/US2019/019687, filed Feb. 26, 2019, which claims the benefit of U.S. Provisional Patent Application Ser. No. 62/635,276, filed on Feb. 26, 2018, and entitled "QUANTIFYING MULTISCALE COMPETITIVE LANDSCAPES OF CLONAL DIVERSITY IN GLIOBLASTOMA," which is herein incorporated by reference in its entirety.

STATEMENT REGARDING FEDERALLY SPONSORED RESEARCH

This invention was made with government support under CA220378 awarded by the National Institutes of Health. The government has certain rights in the invention.

BACKGROUND

Glioblastoma ("GBM") exhibits profound intratumoral molecular heterogeneity that contributes to treatment resistance and poor survival. Each tumor contains multiple molecularly-distinct subpopulations with different treatment sensitivities. This heterogeneity not only supports the pre-existence of resistant subpopulations, but also communication between subpopulations that further modulates tumorigenicity and resistance.

For instance, a minority tumor subpopulation with EGFRvIII mutation has been shown to potentiate a majority subpopulation with wild-type EGFR, increasing tumor growth, cell survival, and drug resistance. This cooperativity presents implications for improving GBM treatment. Yet, compared to other tumor types, the interactions in GBM remain understudied, particularly among common GBM driver gene alterations.

Tissue sampling is a significant barrier to studying the interactions between molecularly-distinct subpopulations in GBM. Notably, contrast-enhanced MRI ("CE-MRI") routinely guides surgical biopsy and resection of the MRI enhancing core, but fails to address the diverse subpopulations of the surrounding non-enhancing parenchyma (so called "brain around tumor" or "BAT"). These unresected residual subpopulations in BAT represent the main contributors to tumor recurrence and can exhibit different therapeutic targets compared with enhancing biopsies.

SUMMARY OF THE DISCLOSURE

The present disclosure addresses the aforementioned drawbacks by providing a method for constructing and implementing a machine learning model to generate at least one image that depicts spatial patterns of a molecular marker across a region-of-interest in a subject. One or more trained machine learning models are constructed by accessing training data with a computer system, quantifying regional molecular diversity in one or more subjects from the training data, and training one or more machine learning models based on the training data and the quantified regional molecular diversity in the one or more subjects. The training data include magnetic resonance imaging ("MRI") data acquired from the one or more subjects and molecular data determined from biopsies collected from the one or more subjects, wherein the molecular data comprises DNA copy number variation ("CNV") data and exome data. Each machine learning model is trained on the training data to localize molecularly distinct subpopulations and phenotypic niches across a region-of-interest. An image that depicts spatial patterns of a molecular marker across a region-of-interest in a subject is then generated by inputting magnetic resonance images acquired from that subject to the appropriately trained machine learning model (i.e., a machine learning model that has been trained for the molecular marker of interest).

It is another aspect of the present disclosure to provide a method for constructing and implementing a machine learning model to generate at least one image that depicts spatial patterns of a biomarker across a region-of-interest in a subject. The method includes constructing one or more trained machine learning models by accessing training data with a computer system, quantifying regional biomarker diversity in one or more subjects from the training data, and training one or more machine learning models based on the training data and the quantified regional biomarker diversity in the one or more subjects. The training data include imaging data acquired from the one or more subjects and biological feature data determined from biopsies collected from the one or more subjects. Each machine learning model is trained on the training data to localize distinct biomarker subpopulations across a region-of-interest. An image that depicts spatial patterns of a biomarker across a region-of-interest in a subject is then generated by inputting images acquired from that subject to the appropriately trained machine learning model.

It is still another aspect of the present disclosure to provide a method for constructing and implementing a machine learning model to generate at least one image that depicts spatial patterns of spatially resolved data across a spatial or geographical region. The method includes constructing one or more trained machine learning models by accessing training data with a computer system and training the one or more machine learning models based on the training data. In general, the training data include spatial data acquired from one or more spatial regions and localized data collected from spatial samples in the one or more spatial regions. Each machine learning model is trained on the training data to quantify spatial patterns of localized data across a spatial region. Thus, one or more images that depict spatial patterns of localized data across a spatial region are generated by inputting spatially resolved data acquired from the spatial region to the one or more trained machine learning models.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
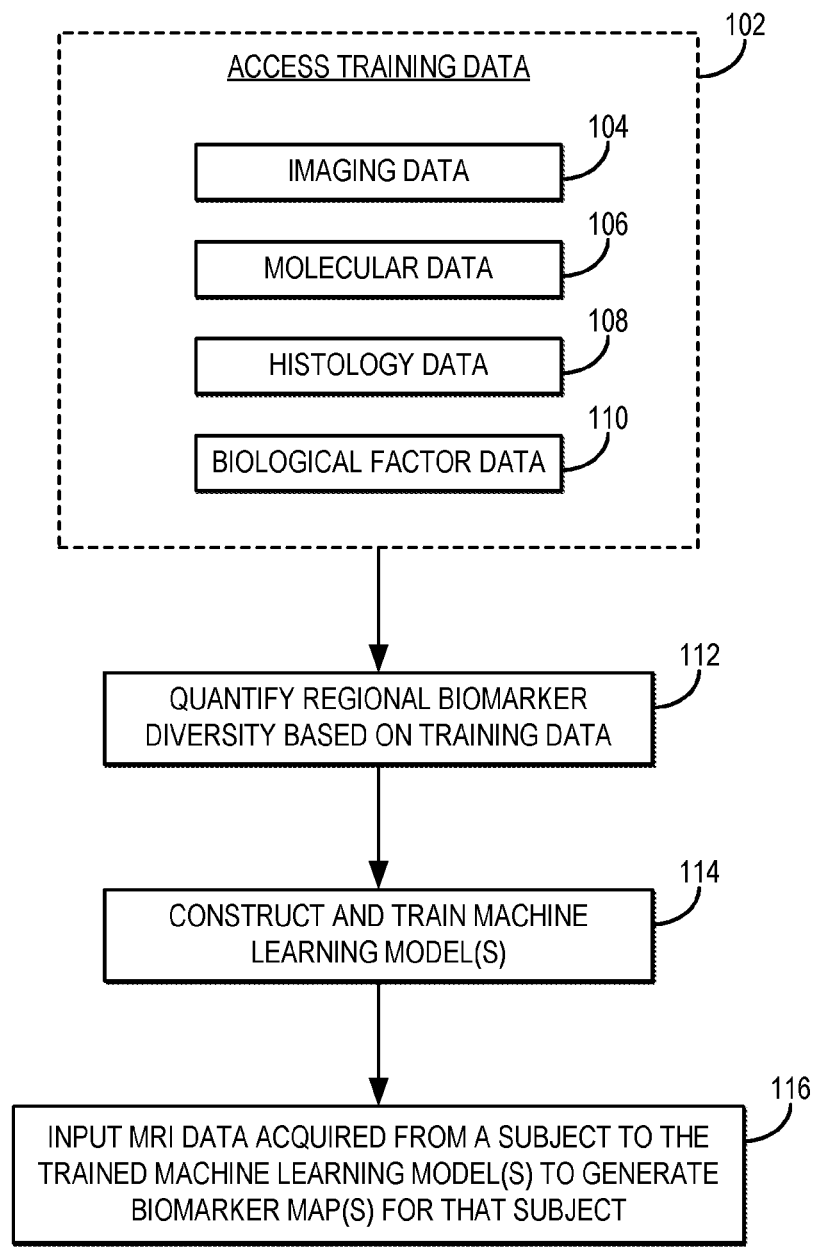
FIG. 1 is a flowchart setting forth the steps of an example method for constructing and implementing trained machine learning models that are trained to generate maps depicting spatial patterns of molecular markers and to quantify regional molecularly distinct subpopulations of tumors and/or regions around tumors

Described here are systems and methods that implement image-guided tissue analysis, MRI-based computational modeling, and imaging informatics to analyze the diversity and dynamics of molecularly-distinct subpopulations and the evolving competitive landscapes in human glioblastoma multiforme ("GBM") or in other tumor types. The interactions between regional molecularly-distinct subpopulations modulate local tumor behavior and regional tumor progression rates. The systems and methods described in the present disclosure construct and implement MRI-based models that can non-invasively quantify this regional molecular diversity and the interactions that modulate progression in GBM, including in the brain around tumor ("BAT") regions.

Imaging techniques can be used to quantitatively characterize tumors in their entirety, including unresected BAT regions. The systems and methods described in the present disclosure use multi-parametric MRI and image-guided biopsies to develop and validate machine learning models of intratumoral heterogeneity, with particular focus on the BAT zone. These MRI-based predictive models can then be stored and used to quantify the intratumoral diversity of molecularly-distinct subpopulations in human GBM by inputting MRI data and other relevant data into the trained predictive models from subjects whose data were not used to build the predictive models.

The systems and methods described in the present disclosure are able to quantify intratumoral diversity in residual tumor populations in the non-enhancing BAT zones of GBM. Tumor populations in the BAT are rarely surgically biopsied or resected, yet they represent the primary targets of adjuvant therapy and the main sources of recurrent disease. Quantifying the interactions between molecularly distinct subpopulations that are unique to this poorly understood tumor segment will help inform future strategies (e.g., adaptive therapy) that target the source of tumor recurrence.

The quantification of molecular and subpopulation diversity provided by the systems and methods described in the present disclosure can be achieved across different spatial scales. Because the predictive models are built on spatially-accurate tissue correlations, the MRI-based models can be extended from single biopsy locations to predict regional diversity across all tumor subregions, including at the intra-biopsy microscopic scale, the regional macroscopic scale, and the dynamic tumor system scale.

Furthermore, the systems and methods described in the present disclosure can be used to quantify the temporal dynamics of molecularly-distinct subpopulation cooperativity and competition over time. The MRI-based predictive models can be applied to serial magnetic resonance images over time to track how common clonal interactions influence tumor behavior, treatment response, and recurrence risk over the course of clinical therapy.

BAT subpopulations represent the primary targets of adjuvant therapy and the main contributors to tumor recurrence. Using MRI to quantify intratumoral heterogeneity and the diversity of molecularly-distinct subpopulations in the BAT can help improve future treatment strategies (e.g., adaptive therapy), particularly under the paradigm of individualized oncology. Previous radiogenomic correlative studies have assigned a single MRI "signature" and genomic profile for an entire tumor, which poorly informs of genomic diversity and spatial heterogeneity within GBM. In contrast, the systems and methods described in the present disclosure identify imaging "signatures" unique to individual voxels in each tumor and BAT zone, drastically increasing spatial resolution to better characterize regional molecular diversity.

In general, the systems and methods described in the present disclosure include collecting image-recorded stereotactic biopsies and quantify the intra-biopsy heterogeneity of molecular markers of interest. These biopsies can be integrated with spatially matched MRI signatures to inform machine learning models that predict spatial patterns of molecular markers across all subregions for the entire tumor. Potential cooperation and competition dynamics can be identified from co-incidence analysis using biopsies and machine learning generated maps. As an example, predicted temporal dynamics of cooperation and competition can be quantified.

It is therefore one aspect of the present disclosure to provide systems and methods for quantifying regional co-existing molecularly-distinct subpopulations and phenotypic niches across the BAT zone of primary GBM. As will be described, GBM tumors can be evaluated at different levels of molecular analysis, such as DNA copy number variants ("CNV"), gene mutation (exome), RNA sequencing ("RNA-seq"), and gene expression.

It is another aspect of the present disclosure to provide systems and methods for implementing MRI-based machine learning models that localize co-existing molecularly-distinct subpopulations and phenotypic niches across BAT. Exome data and intra-biopsy heterogeneity can be used to refine MRI-based machine learning models of regional genomic (e.g., CNV) heterogeneity. Transcriptome (e.g., RNA-seq) data can be used to build MRI-based models of regional phenotype (e.g., hypoxia, proliferation, angiogenesis, invasion). MRI-based models can be used to generate predicted maps over the entire BAT regions, and to localize co-existing molecularly-distinct subpopulations and phenotypic niches. MRI-based models can also be used to quantify combinations of regional molecularly-distinct subpopulations and phenotypic niches that co-localize with regional recurrence in follow-up imaging. As will be described, the predictive models can also be constructed based on biological factor data, such as sex and age. For instance, sex-specific predictive models can be constructed to provide increased predictive accuracy based on the modeling of sex-based differences.

The systems and methods described in the present disclosure have advantageous application to translation studies. The competition and cooperation of molecularly-distinct tumor subpopulations and phenotypic niches can be quantified within the zone of GBM that universally recurs. By providing image-based models that identify the synergistic combinations of molecular subpopulations that are "at risk" for tumor recurrence, the systems and methods described in the present disclosure can elucidate future diagnostic approaches to risk stratify patients based on predicted response in targeted clinical drug trials (e.g., GBM Agile trial). The systems and methods described in the present disclosure can also facilitate new strategies (e.g., adaptive therapy) to exploit clonal co-dependency for therapeutic benefit.

Each GBM can include multiple molecularly-distinct subpopulations that influence treatment sensitivity and local phenotype. This molecular diversity fosters the pre-existence of resistant subpopulations, but also promotes interactions between neighboring subpopulations that further modulate tumorigenicity and resistance. For instance, GBMs may exhibit heterogeneous expression of receptor tyrosine kinase ("RTK") aberrations, such as amplification (amp) of epidermal growth factor receptor ("EGFR") and platelet-derived growth factor receptor A ("PDGFRA").

Some studies have shown, for example, that a minority tumor subpopulation expressing EGFRvIII could potentiate a majority subpopulation expressing wild-type EGFR to increase tumor growth, cell survival, and drug resistance. Other studies have observed cooperativity among heterogeneous subpopulations expressing either EGFRamp or PDGFRamp, such that combined inhibition of both kinases was needed to attenuate phosphoinositide 3-kinase ("PI(3)K") pathway activity in vitro. These interactions between subpopulations create challenges for current treatment paradigms and clinical trials focusing on single drug targets (e.g., EGFR).

It would also be advantageous to quantify the tumor-tumor interactions for other common GBM driver aberrations (e.g., c-MET, PTEN, CDKN2A). Curating these interactions will facilitate promising new approaches (e.g., adaptive therapy) to exploit the codependency and/or competition among molecularly-distinct subpopulations for therapeutic benefit.

Contrast-enhanced MRI (CE-MRI) represents the clinical standard for neuronavigation and routinely guides surgical biopsies from the MRI enhancing tumor segment. Unfortunately, biopsies from enhancing tumor regions fail to address the diverse molecularly-distinct subpopulations that extend beyond the enhancement into surrounding non-enhancing parenchyma (so called "brain around tumor" or BAT). These residual BAT subpopulations can exhibit different therapeutic targets (and interactions) compared with biopsies from the enhancing core. More importantly, BAT subpopulations represent the primary targets of adjuvant therapy and the main contributors to tumor recurrence. Quantification of the diversity and interactions among molecularly-distinct subpopulations in the BAT can help improve future treatment strategies (such as adaptive therapy), under the paradigm of individualized oncology.

Unlike surgical sampling, MRI can help visualize entire tumor volumes, including BAT regions that remain unresected. Further, MRI can measure a variety of complementary biophysical features that reflect regional tumor phenotypes. On CE-MRI, enhancement reflects regions of disrupted blood brain barrier (BBB), while T2W signal demarcates regions of high water content and tumoral edema in BAT. Advanced MRI features include tumor cell density on diffusion-weighted imaging (DWI) white matter infiltration on diffusion tensor imaging (DTI), and microvessel morphology on Dynamic Susceptibility-weighted contrast-enhanced perfusion MRI (DSCpMRI). In addition, MRI spatially encodes signal intensity values for all voxels contained in each image. The textural patterns between voxel intensities and their surrounding neighbors provide further insight to tissue microstructure and phenotypic heterogeneity within the local environment. These complementary MRI features/phenotypes offer potential biomarkers of underlying genomic and transcriptomic status, and have been previously correlated with molecular profiles from GBM. Unfortunately, none of the studies to date have specifically evaluated intratumoral molecular heterogeneity or quantified the regional diversity of molecularly-distinct tumor subpopulations.

Multiple molecularly distinct subpopulations can co-exist within the BAT of a single GBM tumor, and these subpopulations can exhibit distinct MRI-based signatures depending on the phenotypic expression of their underlying genetic aberrations. These MRI-based signatures can be extracted primarily from texture analysis, which improves ML model accuracy and correlation with genetic aberrations, compared to using raw MRI signal values alone.

As mentioned above, the systems and methods described in the present disclosure use image-recorded stereotactic biopsies to build spatially accurate predictive models of regional molecular diversity and tumor-tumor cooperativity/competition. Spatially matching biopsy locations with co-registered MRI measurements maximizes correlation accuracy between tissue analysis (e.g., genetic, histologic) and MRI-based signatures.

To this end, the predictive models generated using machine learning algorithms can be trained on training data that includes magnetic resonance imaging ("MRI") data, histology data, molecular data, biological factor data, or combinations thereof. The histology data and molecular data are estimated, computed, or otherwise determined from spatially annotated biopsies that can be spatially co-registered with the MRI data.

As noted above, each biopsy specimen and sub-specimen can be classified based on molecular data, such as molecular profiles. Molecular subpopulations can be defined using only CNV data, using both CNV and exome (e.g., mutation) data, or combinations of other molecular data. As also described above, the intra-biopsy heterogeneity across the biopsy sub-specimens can also be quantified (e.g., over a range of 0 to 1) for each given molecular marker. In brief, 0 denotes complete absence of the marker across all biopsy sub-specimens, 1 denotes presence of the molecular marker across all biopsy sub-specimens, and an "admixed" category denotes that only some but not all of the sub-specimens express the molecular marker.

In general, the machine learning model can be constructed based on molecular classifications (e.g., 0, 1, admixed) from each biopsy specimen, sub-specimen, or both, and the corresponding spatially matched MRI-based features. In other instances, the molecular features, biological features, or both, can be quantified as one or more continuous variables rather than as discrete classifications or categories. The machine learning model can also be constructed based on regional phenotypic niches for each biopsy specimen, sub-specimen, or both. Phenotypic niches (e.g., hypoxia, angiogenesis, cell proliferation, cell invasion) can be classified based on RNA-sequencing data and GSEA. Intra-biopsy heterogeneity can be defined across each sub-specimen as described above.

Referring now to FIG. 1, a flowchart is illustrated as setting forth the steps of an example method for constructing and implementing a machine learning model (or algorithm) that is trained to quantify regional biological diversity in a region-of-interest in a subject, such as a BAT region. In some instances, the trained machine learning model by generate output as one or more images that depict spatial patterns of one or more biomarkers across the region (e.g., BAT, tumor, or other tissue region). In general, a different machine learning model can be trained for each biomarker. Furthermore, a different machine learning model can be trained for different biological factors, such as one machine learning model for females trained on training data collected from female subjects, and one machine learning model for males trained on training data collected from male subjects.

Although the method described below with respect to FIG. 1 relates to quantifying the regional diversity of molecular markers (e.g., genomic markers, phenotypic markers), it will be appreciated by those skilled in the art that the systems and methods described in the present disclosure can also be more generally applied to quantifying biomarkers other than just genomic or phenotypic markers. For instance, the regional diversity of any suitable biological feature over a tissue or other anatomical region can be quantified by training an appropriate machine learning model using imaging data and spatially resolved data that are associated with the biological feature. For instance, the biological feature could include physiological, biochemical, or histological information (e.g., cell density or other histological features such as those described in the present disclosure) collected from biopsy specimens. As another example, the biomarker may include biological descriptors such as tumor aggressiveness, tumor subtype, or likelihood of recurrence. The biomarker may also include or otherwise indicate interactions between diverse subpopulations of a tissue region (e.g., tumor, BAT region). For instance, the biomarker may include or otherwise indicate cell and/or generic interactions between diverse (e.g., molecularly diverse) subpopulations in a tumor or BAT region. Examples of such interactions are described below with respect to Table 1.

The method includes accessing training data from a memory or other data storage device or medium, as indicated generally at process block 102. This may include accessing imaging data as indicated at process block 104, molecular data as indicated at process block 106, histology data as indicated at process block 108, and/or biological factor data as indicated at process block 110.

As a non-limiting example, imaging data can be collected from subjects (e.g., subjects with stereotactic biopsies) by acquiring images, such as preoperative multi-parametric magnetic resonance images or other medical images (e.g., ultrasound, CT, PET). Thus, in some instances the imaging data may include MRI data. Spatially annotated stereotactic biopsies are also collected from across diverse locations, particularly in the BAT.

MRI data can include magnetic resonance images, parametric maps, texture feature maps, or combinations thereof. Examples of magnetic resonance images include T1-weighted images, contrast-enhanced T1-weighted images, T2-weighted images (e.g., T2-weighted fluid attenuation inversion recovery ("FLAIR") images), T2*-weighted images, diffusion-weighted images, susceptibility-weighted images, and so on.

Parametric maps generally include qualitative or quantitative parameter maps generated from magnetic resonance images. Examples of parametric maps include relative cerebral blood volume ("rCBV"), relative cerebral blood flow ("rCBF"), apparent diffusion coefficient ("ADC"), mean diffusivity ("MD"), fractional anisotropy ("FA"), and so on.

Texture feature maps can include maps depicting texture features generated from magnetic resonance images, parametric maps, or both. For instance, texture features may include first-order statistics or second-order statistics computed from magnetic resonance images, parametric maps, or both. As one general example, texture feature maps can depict texture features computed based on a gray-level co-occurrence matrix ("GLCM"), or may include other texture features known to those skilled in the art. Examples of texture features include energy, entropy, contrast, homogeneity, and correlation. Other examples of texture features may include autocorrelation, cluster prominence, cluster shade, dissimilarity, and so on. Texture features may also include local binary patterns ("LBP"), discrete orthonormal Stockwell transform ("DOST") based texture features, Gabor filter-based texture features, raw mean, and raw standard deviation. In some instances, principal components of the texture feature maps can be computed using a principal component analysis ("PCA") and the principal components can be implemented as training data to be correlated with molecular status.

As one non-limiting example, the MRI data are multi-parametric data that include six different image types: post-contrast T1-weighted images ("T1+C"), T2-weighted images ("T2W"), relative cerebral blood volume ("rCBV") on dynamic susceptibility contrast ("DSC") perfusion, post-contrast T2*-weighted images ("EPI+C"), mean diffusivity ("MD"), and fractional anisotropy ("FA"). These MRI contrasts provide regional physiologic metrics of the tumor microenvironment, including vascular leakage and blood-brain barrier ("BBB") disruption (T1+C); vasogenic and tumoral edema (T2W); microvessel volume and angiogenesis (rCBV); tumor cell density and cell size (EPI+C); cell density and proliferation (MD); and white matter integrity and tumoral infiltration (FA).

As a non-limiting example, regions-of-interest for all co-registered MRIs measuring 8×8×1 voxels at each biopsy location that roughly correspond to the target volume of each tissue specimen (~250 mg) are generated. For image analysis, mean and standard deviation of gray level intensities and map intensity values within each ROI can be measured and mapped onto the range 0-255. This step helps standardize intensities between ROIs and reduces effects of intensity non-uniformity on features extracted during subsequent texture analysis. Next, texture analysis can be performed as described above. As one example, three complementary algorithms can be used: GLCM, LBP, and DOST. In one example study, 240 MRI-texture features and 16 raw features (i.e., mean and SD for 8 MRI contrasts) were generated from each ROI. The principal components (PCs) for respective MRI-texture algorithms (GLCM, LBP, DOST) for each ROI were then determined. Each PC will correlate individually with molecular status as described below.

For each spatially annotated biopsy, molecular data are also collected. Molecular data can include DNA copy number variants ("CNV"), gene mutation (exome), RNA sequencing ("RNA-seq"), gene expression, proteomics analysis data, and so on. These molecular data can be determined from the biopsies and spatially matched to the imaging data.

As noted above, the biopsy specimens can be divided into separate sub-specimens to also assess the degree of genetic/molecular heterogeneity within individual biopsy specimens.

Tumoral DNA/RNA analytes can be isolated and multi-level molecular analysis performed for all biopsy specimens and/or divided biopsy sub-specimens. Whole exome sequencing ("WES") and RNA-seq can be performed to assess the mutation profile and to quantify transcripts. Somatic coding mutations (e.g., ~90 Gb, 30× coverage) and gene expression (e.g., 100 million reads) can also be collected.

As a non-limiting example, molecular markers associated with frequent key GBM drivers (e.g., EGFR, PDGFRA, PTEN) can be assessed. Additionally or alternatively, NF1, TP53, CDKN2A, RB!, ATRX, MET, MGMT, and mutations in the TERT promoter can also be evaluated. RNA sequencing data can be used to validate gene mutation (exome) profiles.

Genomic data (e.g., CNV, exome) can be used to classify molecularly-distinct subpopulations within each biopsy and RNA-seq can be used to quantify phenotypic niches (e.g., hypoxia, proliferation, angiogenesis, invasion) for each biopsy. Parameters such as co-existence and heterogeneity of molecularly-distinct subpopulations and phenotypic niches can be quantified within each biopsy. Combinations of molecularly-distinct subpopulations and enriched phenotypic niches in regions of recurrence can also be identified.

As one non-limiting example, molecular data can be estimated, computed, or otherwise determined using one or more of the following analysis techniques or other analysis techniques known to those skilled in the art. Germline and somatic variants can be determined from WES data. For instance, WES profiles from a subject's white blood cells for each PDX model can serve as germline references for detection of somatic mutations. RNA-seq can be determined using an analysis pipeline that includes mapping, read count generation, and junction detection. Differential gene expression analysis can be implemented between rim and core samples. Integrative analysis of genomic and transcriptomic data can be performed using a least absolute shrinkage and selection operator ("LASSO")-type regularization method. Hierarchical/consensus clustering and principal components analysis ("PCA") can be used to identify genomic heterogeneity in the invasive population. Ontology analyses can be employed to define biological processes, and gene set enrichment analysis ("GSEA") can be used for comparisons of gene signatures in the biopsy specimens to assess Cancer Hallmark Pathways. Hypoxia, angiogenesis, cell proliferation, and cell invasion gene signatures from RNA-seq can be curated and used to quantify the phenotypic niches in each sample using Gene Set Variation Analysis ("GSVA").

As noted above, additional or alternative molecular analysis techniques can also be implemented and used to collect molecular data from the spatially annotated biopsies.

In some instances, the molecular data can include a classification of tumor subpopulations based on the molecular analysis of the spatially annotated biopsies. For instance, classification of tumor subpopulations can be performed based on distinct molecular profiles. For each biopsy specimen, biopsy sub-specimen, or both, the shared commonality of aberrant CNV and gene mutation of key GBM drivers (e.g., those described above) can be used to define molecularly-distinct populations within each spatially annotated biopsy specimen (e.g., tissue sample) or sub-specimen.

PyClone plots, or other statistical models that can infer the prevalence of point mutations in heterogeneous tissue samples, can also be used to integrate molecular data and summarize subpopulation identity. PyClone is described for example by A. Roth, et al., "PyClone: Statistical Inference of Clonal Population Structure in Cancer," *Nature Methods*, 2014; 11:396-398.

As one non-limiting example, CNV, which is used to inform the PyClone priors, can be detected based on a log2 comparison of normalized physical coverage (or clonal coverage) across tumor and normal sequencing data. Somatic mutations and allelic abundance can be called using three variant callers: Mutect, Strelka, and Seurat, and then consensus variants can be gathered as input to PyClone.

Additionally or alternatively, molecular data can include an estimate of tumor content derived from copy number alteration or from pathologist estimates, which can be supplied to ensure more accurate inference of clonal population.

For each spatially annotated biopsy, histology data can be collected. In general, histology data can include qualitative or quantitative histological features determined, estimated, or computed from or based on the spatially annotated biopsies. By way of example, the histological features can generally include quantitative information derived from histological samples. For example, the histological features can be associated with the size, shape, area, or number of cells, including separate measurements for different cell types.

As one non-limiting example, the histological feature can be cell density, which is a measurement of the number of cells in a given volume of tissue. As another example, the histological feature can be voxel-wise percentage of necrosis or vascularity.

As another non-limiting example, histological features can include quantitative information derived from staining. For instance, the histological features can be associated with the presence of different colors in a sample, the area of a given color in a sample, the relative proportions of different colors in a sample, or the intensity of one or more colors in a sample.

In some instances, the stain can an immunohistochemical stain with cell-type specific markers for stromal cell types (e.g., reactive astrocytes, activated microglia). In these instances, the histological features can include quantitative information about the cellular (e.g., stromal) milieu.

When the stain is a fluorescent molecule, the histological feature may include quantifiable information derived from fluorescent imaging of the histological sample, such as fluorescence intensity. As an example, the histological feature can be any characteristic that can be quantified or labeled from histology using a microscope or other tool for evaluating tissue slides.

One example of how histological features can be obtained is now described. Tissue samples that have been previously imaged can be stained. As one example, the samples can be stained using an H&E stain, an immunohistochemical stain, or so on. Each tissue slide can then be photographed across the entire sample. For instance, a motorized microscope stage can be used to obtain photographs of the stained slides. In some instances, each photograph can be processed individually and stitched together to form a histology image of the tissue sample.

Additional processing can be performed on the histology image as necessary or desired. For example, to obtain a cell density measurement, thresholds for segmentation of cell nuclei can be applied and, following segmentation, the nuclei in each histology image can be counted to obtain a voxel-wise measurement of cell density. In some other embodiments, a clustering algorithm can be applied to segment the histology image. For instance, a k-means clustering algorithm can be applied to each histology image for segmentation of cell nuclei and anatomical features.

By way of example, spatially annotated biopsies can be provided and segmented into histology tissue types, histological features, or both, and then co-registered to the MRI data.

In some instances, the spatially annotated biopsies can be divided into separate sub-specimens to assess the degree of histological feature homogeneity or heterogeneity within individual biopsy specimens. As one example, the spatially annotated biopsies can be divided into quarters.

Biological factor data may include information such as the subject's sex (e.g., male, female), age, and so on. It will be appreciated by those skilled in the art that the training data may also include morphological data or any other qualitative or quantitative descriptor of the biopsy specimens or sub-specimens.

Referring still to FIG. 1, using the molecular data, regional molecular diversity in the plurality of subjects from which the training data have been collected is quantified, as indicated at step 112. For instance, based on the molecular data, the co-existence and heterogeneity of molecularly-distinct subpopulations within each biopsy can be quantified. In some instances, this can include quantifying intra-specimen heterogeneity. Genomic identity can be determined (e.g., based on CNV and exome) for each biopsy sub-specimen to assess the degree of consistency/agreement across all sub-specimens. Although this may not represent single cell level heterogeneity, these data can provide insight into the heterogeneity observed at the scale of a sub-specimen (e.g., 250 mg in some instances) biopsy. This provides the additional benefit of increasing sensitivity of detecting specific molecular markers within the biopsy specimen.

For any given molecular marker, the heterogeneity of that single marker can be represented from 0 to 1 to denote being present in none, some, or all of the sub-specimens (e.g., none, one-quarter, one-half, three-quarters, or all four segments when biopsy is divided into quarters). To further quantify the heterogeneity within each biopsy a Shannon index, $$H = -\sum_{i=1}^{N} p_i \ln(p_i),$$

where in this case $p_i$ is the proportion of the biopsy belonging to a molecularly distinct subpopulation, i, and there are N total subpopulations. Analysis with PyClone can provide the proportions, $p_i$, for the various subpopulations.

After the Shannon index is computed for each biopsy, these values can be compared across multiple biopsies within each subject. The Shannon index values can also be compared across different subjects using descriptive statistics. Possible correlations with spatial locations on the MRI can be examined (e.g., is there a predominance for higher diversity in certain BAT regions).

In some instances, quantifying the co-existence and heterogeneity of molecularly-distinct subpopulations within each biopsy can include quantifying correlations between markers. As an example, for each subject, and for each pair of molecular markers, a chi-square test can be used quantify the significance of any spatial association between the markers. The sign of the associated correlation coefficient can be suggestive of cooperative (+) or competitive (−) dynamics of the subpopulations.

Quantifying the co-existence and heterogeneity of molecularly-distinct subpopulations within each biopsy can also include identifying combinations of molecularly-distinct subpopulations and enriched phenotypic niches in regions of recurrence. In these instances, subjects from whom data are collected will undergo therapy, such as standard adjuvant therapy (e.g., Stupp protocol). Serial multi-parametric MRI data are acquired from these subjects during and after the adjuvant therapy to evaluate for MRI-enhancing lesions that indicate tumor recurrence. Upon development of enhancing recurrent lesions on MRI in each subject, the regions-of-interest ("ROIs") will be segmented to encompass the recurrent lesions. The surveillance MRI data (showing the recurrence) can then be coregistered with the initial surgical MRI data (used to spatially annotate biopsy locations in the primary GBM tumor). The images can then be overlaid to determine which biopsy specimens (and corresponding molecular profiles and MGMT methylation status) spatially co-localize with the region of recurrence. Further, the time to progression ("TTP") for each region of recurrence, which gives an indication of the recurrent tumor growth rate, can be determined. TTP can be quantified as the amount of time needed to manifest tumor recurrence within a specific region of the BAT. As such, the incidence and rate of recurrent tumor growth for molecularly-distinct subpopulations and associated niches as defined by the molecular profiles can be quantified within each biopsy specimen.

In some instances, these subjects can undergo surgical re-resection/re-biopsy of recurrent lesions. In these cases, pre-operative multiparametric MRI and spatially annotated stereotactic biopsies can be further acquired from the regions of tumor recurrence. As described above, the tissue samples may also be divided in into sub-specimens. Molecular analyses can then be performed to collect additional molecular data for these subjects in the recurrent regions.

To confirm that MRI enhancement represents tumor recurrence (as opposed to post-treatment effect), the presence of tumor recurrence can be evaluated using a perfusion MRI Fractional Tumor Burden ("FTB") method, as described by L. Hu, et al., in "Reevaluating the Imaging Definition of Tumor Progression: Perfusion MRI Quantifies Recurrent Glioblastoma Tumor Fraction, Pseudoprogression, and Radiation Necrosis to Predict Survival," *Neuro. Oncol.*, 2012; 14:919-930, or using other evaluative methods.

As described above, quantifying regional molecular diversity can also include building a three-class classifier based on the 0, 1, and admixed classes that denote the absence, presence, or admixture of molecular markers across biopsy sub-specimens. Exome data can be incorporated to refine the quantification of the heterogeneity status for each biopsy sample.

Referring still to FIG. 1, a machine learning model is then trained using the training data and the quantified molecular diversity, as indicated at step 114. The machine learning algorithms used can include machine learning algorithms known to those skilled in the art. For instance, a Principal Component Analysis ("PCA") can be used for dimension reduction of texture features. Machine learning algorithms that can be used to build classifiers between MRI features and molecular markers can include Support Vector Machines ("SVM"), Linear Discriminant Analysis ("LDA"), Quadratic Discriminant Analysis ("QDA"), Decision Tree ("DT"), and so on. In some instances, the machine learning model may implement an active learning model or a transfer learning model.

As noted above, a different machine learning model can be trained for each combination of molecular marker and biological factor. For instance, a different machine learning model can be trained for each molecular marker of interest for a first biological factor, and then another machine learning model can be trained for each molecular marker of interest for a second biological factor. In this way, biological factor-specific machine learning models can be trained for each desired molecular marker. For instance, female-specific and male-specific machine learning models can be trained.

Molecular markers can refer to genomic markers (e.g., EGFR, PDGFRA, PTEN, NF1, TP53, CDKN2A, RB1, ATRX, or MET), phenotypic markers (e.g., hypoxia, angiogenesis, cell proliferation, cell invasion), or both.

The trained machine learning models are implemented to generate one or more images that depict regional molecular diversity by applying MRI data acquired from a new subject to the one or more trained machine learning models, as indicated at step 116. For instance, multi-parametric MRI data can be input to the different trained machine learning models to generate separate maps for the molecularly-defined classifications defined above. These maps will display probabilities for each voxel regarding whether there is high or low confidence that the voxel corresponds to the presence of the particular molecular subpopulation of interest. This process can be repeated to generate maps for a panel of molecularly-distinct classifications. The molecular classification MRI-based ML maps can then be combined (e.g., by overlaying on each other) in order to generate a single image that depicts co-existing molecularly distinct subpopulations and/or phenotypic niches.

As noted above, in some examples the trained machine learning models may implement a transfer learning model. In these instances, imaging data and initial tissue data (e.g., biopsy data) collected from the subject can be input to the trained machine learning models. Such models can be used to predict spatial patterns of biomarkers (e.g., molecular markers) throughout a tissue region (e.g., a tumor, a BAT region, other brain tissue regions) for subsequent biopsies as well as regions that have not been or will not be biopsied in the subject. These embodiments can also be facilitated by adding the ability to input biological/molecular data as a continuous variable (e.g., not just categorical of 0, 1, admixed). Examples of transfer learning models that can be implemented are described, for example, in co-pending Patent Application No. PCT/US2018/061887, which is herein incorporated by reference in its entirety.

Thus, using the systems and methods described in the present disclosure one machine learning model can be trained for each molecular marker (e.g., genomic/phenotypic marker) using MRI data. As noted, machine learning models can be separately trained for different biological factors, such as sex or age. As an example, a machine learning classifier can be trained using texture features of an ROI at each biopsy location and the heterogeneity status of the molecular marker (e.g., the genomic/phenotypic marker) of the biopsy. Machine learning algorithms (e.g., SVM, LDA, QDA, DT) can be used to build this classifier.

These trained machine learning models can then be used to generate probabilistic maps for molecular marker (e.g., genomic/phenotypic marker) status across the BAT. Furthermore, a classifier can be used to generate a prediction for each window sliding over the entire BAT (with one pixel offset between successive windows) using the texture features computed for that window. As an example, the window can be an 8×8 window. In this way, a predictive map for the BAT can be generated. A predictive map can be generated for each genomic and phenotypic marker of interest. As noted above, the prediction can be a probabilistic score quantifying the certainty/uncertainty for marker existence within each localized region across the entire tumor, including the BAT zone. In this way, the spatial heterogeneity of genomic subpopulations and phenotypic niches within BAT can be quantified.

Figure 2:
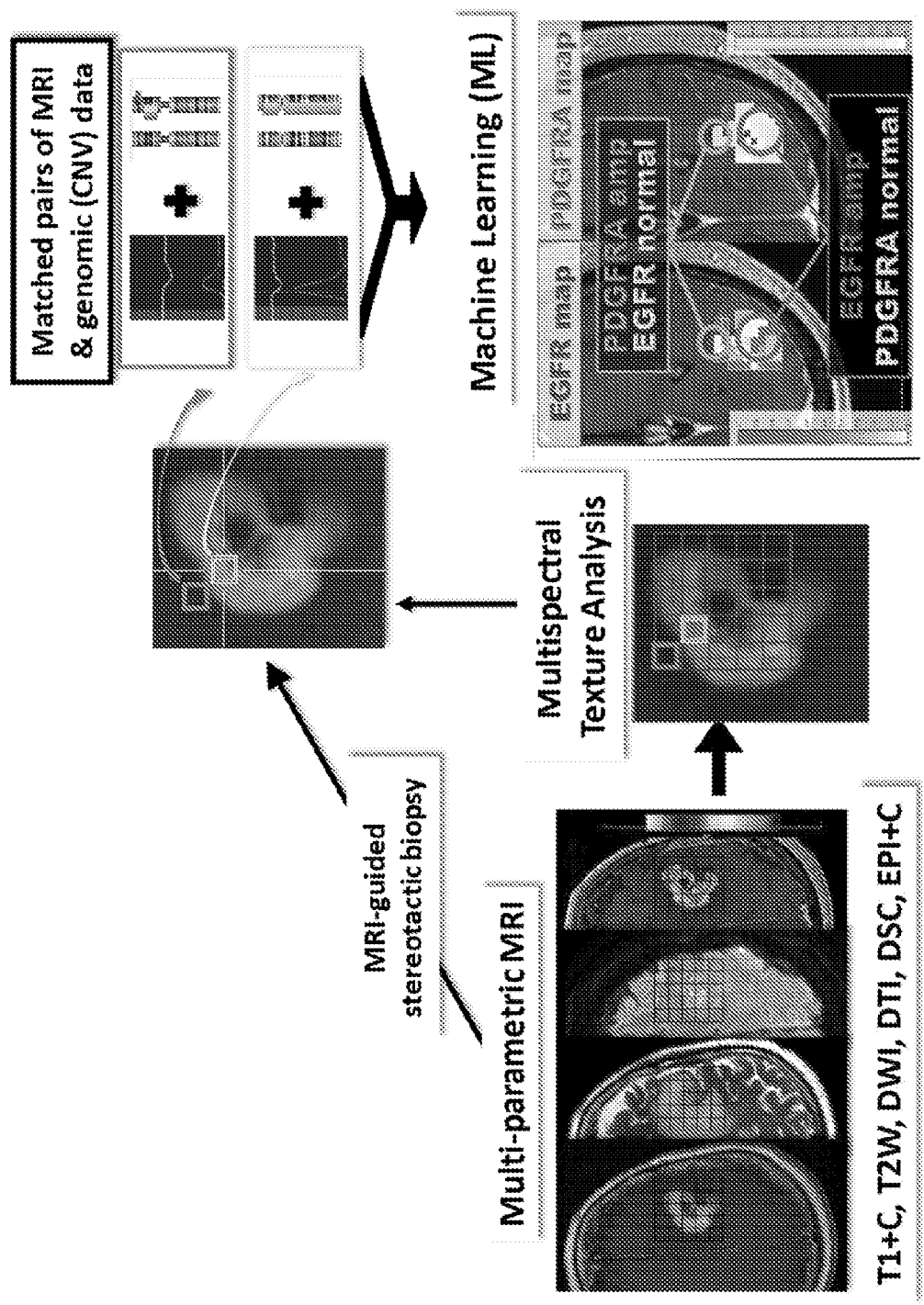
FIG. 2 is an example workflow implementation of the method of FIG. 1.

An example workflow of constructing and implementing a machine learning model according to some embodiments described in the present disclosure is shown in FIG. 2.

As described above, the systems and methods described in the present disclosure are advantageous for translational imaging. For instance, regional recurrence on serial surveillance MRI can be defined and coregistered images with initial surgical multi-parametric MRI data. This enables ML predictive maps of molecularly distinct subpopulations and regional phenotypes to be overlaid to quantify combinations that co-localize to regional recurrence. Regional variations in TTP that indicate recurrent tumor growth rates associated with local molecularly-distinct subpopulations and co-localized phenotypic niches can also be determined.

It is contemplated that BAT will demonstrate specific patterns of subsequent recurrence on serial surveillance multi-parametric MRI. The TTP, or the amount of time needed to manifest tumor recurrence within a specific region of the BAT, can be quantified to further guide such analyses.

Using the systems and methods described in the present disclosure, MRI-based maps of molecularly-distinct subpopulations (based on the surgical MRI) can be co-localized within the corresponding spatial locations of regional tumor recurrence. By further overlaying MRI-based ML maps of regional phenotype, combinations of molecularly-distinct subpopulations and phenotypic niches that enrich for regional recurrence can be identified. The incidence and rate of recurrent tumor growth for the molecularly-distinct subpopulations and associated phenotypic niches can also be quantified. As another example use, in a subset of recurrent GBM patients undergoing stereotactic biopsy and measurement of spatially matched MRI metrics, spatially matched primary and recurrent genomic subpopulations can be matched to model local evolution of molecularly-distinct subpopulations.

Using the systems and methods described in the present disclosure molecularly-distinct subpopulation and phenotypic niche interactions predicted by clinical GBM data can be evaluated using PDX models in vitro and in vivo with appropriate molecularly defined subpopulations. PDX models can be used to quantify and assess the competition and cooperative dynamics of tumor subpopulations with genetic markers of interest.

Intracranial implantation of the PDX in mice gives rise to tumors typical of patient GBM including nuclear atypia, vascular involvement in tumor core, and significant invasion at the tumor/normal brain interface. These models can be used to quantify the cooperative/competitive dynamics among molecularly-distinct subpopulations. For these analyses, relevant biological variables can be separately accounted for. For instance, biological variables such as age and sex of the patients contributing the PDX cell lines can be recorded.

As one example, in vitro data may include a panel of primary GBM xenograft cell lines with the appropriate genetic markers based on those identified in human GBM tumors. This may involve key GBM driver alterations, such as EGFR and PDGFRA amp. For example, GBM8 (EGFR wildtype amp) and GBM85 (PDGFRAamp) can be utilized to quantify the co-existence of these molecularly-distinct subpopulations. As new subpopulations are identified and characterized using the systems and methods described in the present disclosure, appropriate PDX cell models can be chosen to test the cooperative and competitive natures.

As one example study design, to enable co-expression of two reporter genes in each xenograft cell line, a 2A peptide enabled lentiviral construct encoding Firefly Luciferase (FLuc) and RFP (FLuc-T2A-RFP; Biosettia) or a lentiviral construct encoding *Renilla* Luciferase and green fluorescent protein (RLuc-T2A-GFP; GenTarget Inc.) can be used. GBM8 can be infected with lentiviruses expressing FLuc-T2A-RFP, and GBM85 can be infected with lentiviruses expressing RLuc-GFP. Positively transduced GBM8 and GBM85 cells can be enriched (>98%) by FACS sorting, expanded by growth as orthotopic flank tumors in mice, and cryopreserved for use in proposed studies. Cell growth and motility can be performed on the molecularly defined PDX cells alone and in co-culture conditions to assess competition and cooperation. For cell growth assays, CellTiterGlo (Promega) can be used. Secondary assays in 2D can include a multiplexed BrdU (DNA synthesis) and Ki-67 (resting/cycling) assay, which more specifically quantifies cell proliferation. Further refinement, as needed, can be carried out using assay conditions with limiting growth factors to assess competition or synergy of the co-cultured subpopulations. In parallel, the in vitro bioluminescence for each cell line alone and in combination can be assessed to determine the correlation between cell number and the bioluminescence signal. Cells can be seeded at different concentrations and substrates for each luciferase (1 µg/ml coelenterazine for Rluc and 1.5 µg/ml D-luciferin for Fluc) can be added to the medium. Luciferase activity can be measured using a microplate reader at the appropriate wavelength. For cell motility assay ("Migration/Invasion"), cell migration can be assessed using the uncoated Transwell Boyden Chamber assay, whereas cell invasion can be assessed in the Boyden Chamber Matrigel invasion assay, wherein laminin-rich matrix serves as a good surrogate for brain stroma. Cells migrating through the chamber can be quantified by blinded observers.

As another example study design, primary GBM xenograft cell lines with the appropriate genetic markers based on those identified in the human GBM tumors can be selected. For instance, with EGFR and PDGFRA amplifications, intracranial xenografts can be established in nude mice. Mice can be randomized to groups of 10 and can receive GBM8-FLuc-T2A-RFP or GBM85-RLuc-GFP neurosphere cells. Cells (300,000) can be stereotactically implanted into right basal ganglia. For co-culture experiments, equal cell numbers of GBM8 and GBM85 can be mixed and the cell mixture implanted. At 2-3 weeks post-implant, two animals from each group can be sacrificed to verify equivalent tumor growth in all groups. For the rest of the animals, mice can be imaged for Rluc activity by injecting coelenterazine (100 µg/animal in 150 µl of saline) intravenously via the tail vein and 5 min later, photon counts can be recorded over 5 min using the IVIS imaging system. To image Fluc, mice can be given intraperitoneal injection of D-luciferin (4.5 mg/animal in 150 µl of saline), and photon counts can be recorded 5 min after D-luciferin administration over 5 min.

The total photon flux (photons/sec) can be measured from a region of interest over the skull using the Living Imaging software. Mice can be imaged every 3 days until reaching a moribund state. Tumor bearing brains can be harvested for serial sectioning and immunohistochemical analysis.

Ex vivo fluorescence imaging on cryosections of tumor bearing brain can be performed. Immediately after sacrificing the animals, the whole brains can be dissected and embedded into O.C.T. Series of coronal sections (15 µm) can be cut from the O.C.T. embedded brain and tumor tissues can be identified by crystal violet staining. The adjacent tissue sections can be used for fluorescence microscopic study. The ex vivo images can be taken by using the living Imaging software as used for the in vivo studies above. Quantification of RFP and GFP cells can be obtained through the common region of interest on both the tumor side and the contralateral normal brain of each image. A total of photon count (counts/s) in the identical region of interest can be used for comparison of dynamic change in signal intensity.

Histology and fluorescence microscopy can also be performed. Brains can be removed from euthanized mice and histological (H&E staining) and immunohistochemical (IHC) analyses performed to assess cell proliferation (Ki-67), cell death (activated caspase-3), and quantification of the population of RFP or GFP cells using fluorescence microscopy. Scoring of IHC can be performed in a semi-quantitative manner. Due to variable number of tumor cells in each of the tissue sections, the percent of tumor cells that stain can be scored as 1 (<5%), 2 (5 to 50%), and 3 (>50%). Stain intensity can be scored as 1 (low), 2 (moderate), or 3 (high). The total IHC score can be the product of the percent cells stained and the stain intensity thereby giving a semi-quantitative range of 1 to 9. A product score >4 can be designated as significant. Analysis of glioma cell spread can be scored from the H&E stained sections on a scale of I-IV according to the following criteria: I—unilateral and well demarcated, II—fuzzy border and/or showing movement into other hemisphere, IIIA—bilateral, but restricted to around midline structures, IIIB—bilateral with clear involvement of both hemispheres, IV—largely replacing the brain.

To investigate the therapy response of PDX to standard first-line therapy of concurrent temozolomide (TMZ) and radiation therapy (RT) followed by adjuvant TMZ can be performed. Briefly, mice with established GBM8 FLuc-RFP, GBM85 RLuc-GFP, or GBM8 FLuc-RFP+GBM85 RLuc-GFP intracranial tumors as assessed by IVIS imaging can be randomized to therapy groups of (1) placebo+RT, (2) TMZ (66 mg/kg daily for 5 days) alone, (3) RT alone (2 Gy twice a day for 5 days), or (4) concomitant TMZ and RT. Mice can be imaged by IVIS twice weekly until reaching a moribund state. Following sacrifice, brains can be resected, embedded, and sectioned for IHC analysis of tumor cell dispersion, cell proliferation, and apoptosis as described above. Correlative fluorescence microscopy of the same sections will positively identify implanted xenograft cells and to determine the relative proportion of PDX in the mixed tumor. Comparison of xenograft survival when implanted alone relative to implantation as a mixed tumor can be analyzed to determine cooperativity in treatment resistance.

Using data collected from in vitro studies, such as those mentioned above, dynamic models for competition/cooperation can be developed. For example, a Lotka-Volterra model describing the interaction between two cell populations can be parameterized. To illustrate this example, PDGFRAamp and EGFRamp can be considered:

$$\frac{dN_{PDGFRA}}{dt} = \frac{r_{PDGFRA}}{K_{PDGFRA}} N_{PDGFRA}(K_{PDGFRA} - N_{PDGFRA} + \alpha_{PE} N_{PDGFRA}); \quad (1)$$

$$\frac{dN_{EGFR}}{dt} = \frac{r_{EGFR}}{K_{EGFR}} N_{EGFR}(K_{EGFR} - N_{EGFR} + \alpha_{EP} N_{EGFR}); \quad (2)$$

where $N_{PDGFRA}$ and $N_{EGFR}$ are the numbers of PDGFRAamp and EGFRamp cells, respectively, which can be determined from cell counts from CellTiterGlo or using other methods; $r_{PDGFRA}$ and $r_{EGFR}$ are growth rates for PDGFRAamp and EGFRamp cells, respectively, which can be determined from BrdU labeling data from in vivo cell cultures; $K_{PDGFRA}$ and $K_{EGFR}$ are carrying capacity for PDGFRAamp and EGFRamp cells, respectively, which can be determined from cell counts in single cell cultures; and $\alpha_{PE}$ and $\alpha_{EP}$ correspond to the effects of PDGFRAamp cells upon EGFRamp cells, and that of EGFRamp cells upon PDGFRAamp cells, respectively, which can be estimated by fitting the model to cell count curves with a nonlinear regression.

Cell counts at multiple time points obtained from in vitro studies can generate experimentally-derived growth curves. Fitting this model to these curves (e.g., with a mixed effects nonlinear regression) can be done to determine the corresponding a parameter values. These will characterize the nature of the relationship between the populations as shown in Table 1 below, with the numeric values of the α's indicating the relative degree of the effects.

TABLE 1

Signs of the α derived from fitting the model to experimental data describe the nature of cell population interactions.

| $\alpha_{PE}$ | $\alpha_{EP}$ | Type of Interaction |
|---|---|---|
| 0 | 0 | neutralism: no negative or positive effects |
| − | 0 | amensalism: P negatively affected by E |
| 0 | − | amensalism: E negatively affected by P |
| + | 0 | commensalism: P positively affected by E |
| 0 | + | commensalism: E positively affected by P |
| − | − | competition |
| + | + | mutualism/cooperation |
| + | − | parasitism: of P upon E |
| − | + | parasitism: of E upon P |

P = PDGFRAamp cells, and E = EGFRamp cells. (+) indicates benefit, (−) indicates cost, and (0) indicates no effect.

This process can be repeated with data from the PDX models described above to characterize the relationship between cells in an in vivo setting, the interactions of cell populations in different environments to be compared and contrasted. This can be achieved by obtaining cell estimates from bioluminescence images, using a conversion factor to relate signal intensity to cell number.

Using the MRI-based models developed using the systems and methods described in the present disclosure, the abundance of molecularly-distinct subpopulations within each tumor can be quantified using multiple serial MRI examinations from the time of primary surgery to the time of tumor recurrence. Specifically, the segmented predicted volume of each molecular subpopulation can be quantified and relative volumetric changes at each imaging time point can be plotted. Tracking the abundance of distinct subpopulations over time can help infer tumor behavior and the cooperative and competitive interactions between subpopulations over the course of therapy.

These dynamics can be validated in a subset of patients undergoing stereotactic biopsy and molecular profiling of recurrent tumor samples to confirm the relative abundance of molecularly-distinct subpopulations corresponding to regional recurrence. In particular, regions of recurrence that are spatially matched to previously biopsied BAT regions can be targeted at the time of primary surgery. In the event that GBM treatment impacts the MRI-based signatures of primary (untreated) GBM, these recurrent biopsy samples and spatially matched MRI measurements can be further used to build MRI predictive models specifically for recurrent tumor in the post-treatment setting, as mentioned above.

Figure 3:
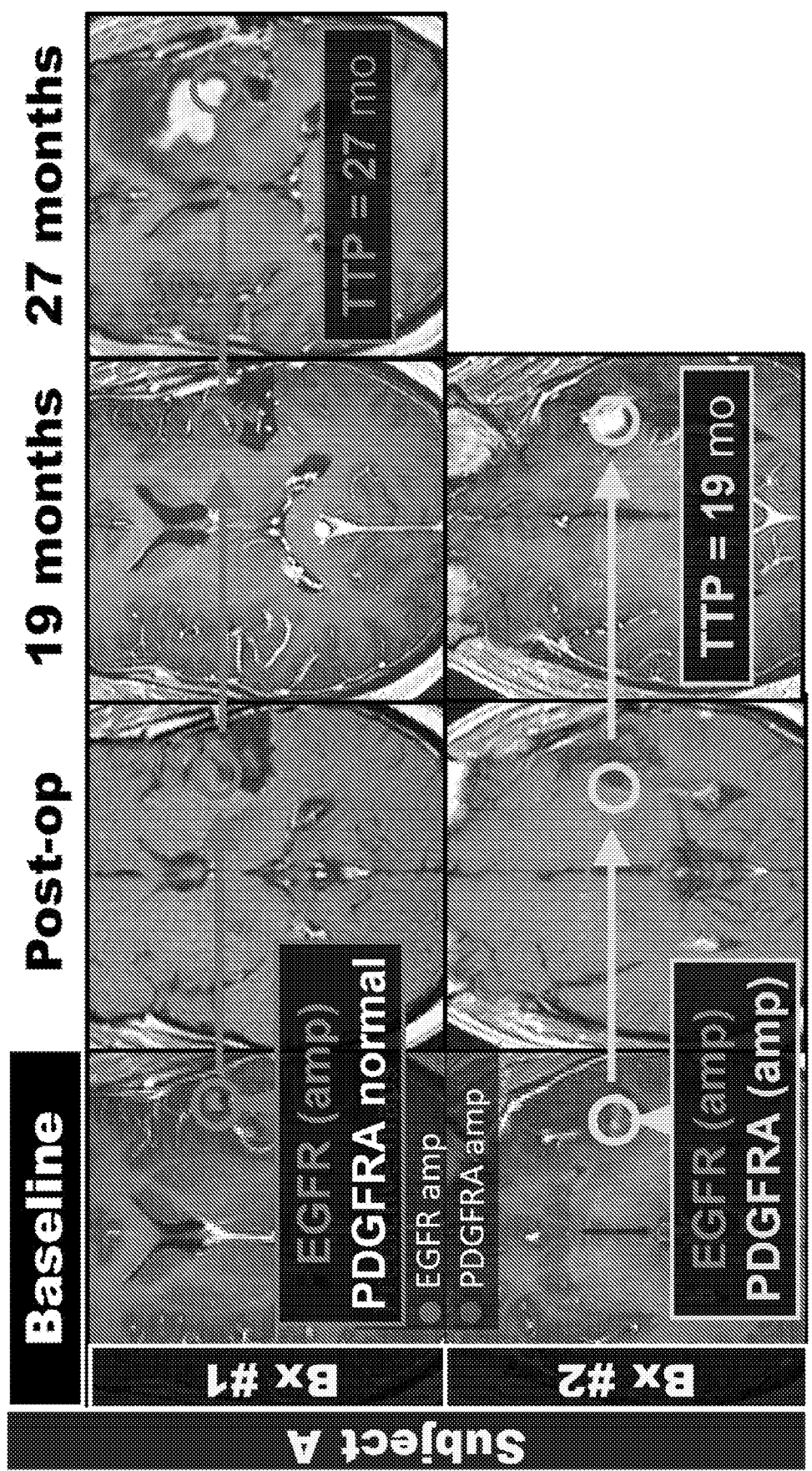
FIG. 3 shows an example where regional molecular combinations exhibit different recurrent patterns in a single GBM patient.

FIG. 3 shows an example where regional molecular combinations exhibit different recurrent patterns in a single GBM patient. Two separate biopsies (Bx #1, Bx #2) were genomically profiled for CMV status in a 57 y/o GBM patient who was subsequently treated with chemo-radiotherapy. Bx #1 (top row, red circle) showed a tumor population with only EGFR amplification (amp). This region did not recur until 27 months after baseline. Meanwhile, Bx #2 (bottom row, green circle) exhibited both EGFRamp and PDGFRamp, which likely represented two molecularly-distinct subpopulations. This region recurred earlier with a time to progression (TTP) of 19 months. These preliminary data suggest that interactions between combinations of molecularly-distinct subpopulations can impact tumor behavior and likelihood of recurrence over time. Therefore, in some embodiments the systems and methods described in the present disclosure can be implemented to generate a report that indicates a likelihood of recurrence over time. In some instances, such a report and include an estimated TTP, which may be estimated based on one or more molecular marker maps generated using one or more trained machine learning models. Additionally or alternatively, such a report may include one or more molecular marker maps generated using one or more trained machine learning models, which can be displayed to a user. In some instances, these maps can be combined into a single map that quantifies or otherwise depicts regional molecular diversity in a region, such as a BAT region, a tumor region, or both. For instance, EGFR and PDGFRA amplified maps at the biopsy regions are depicted in FIG. 3 as being overlaid on the MRI images to illustrate the use of these modeling maps to predict biological activity/response and/or treatment outcome.

Figures 4A, 4B:
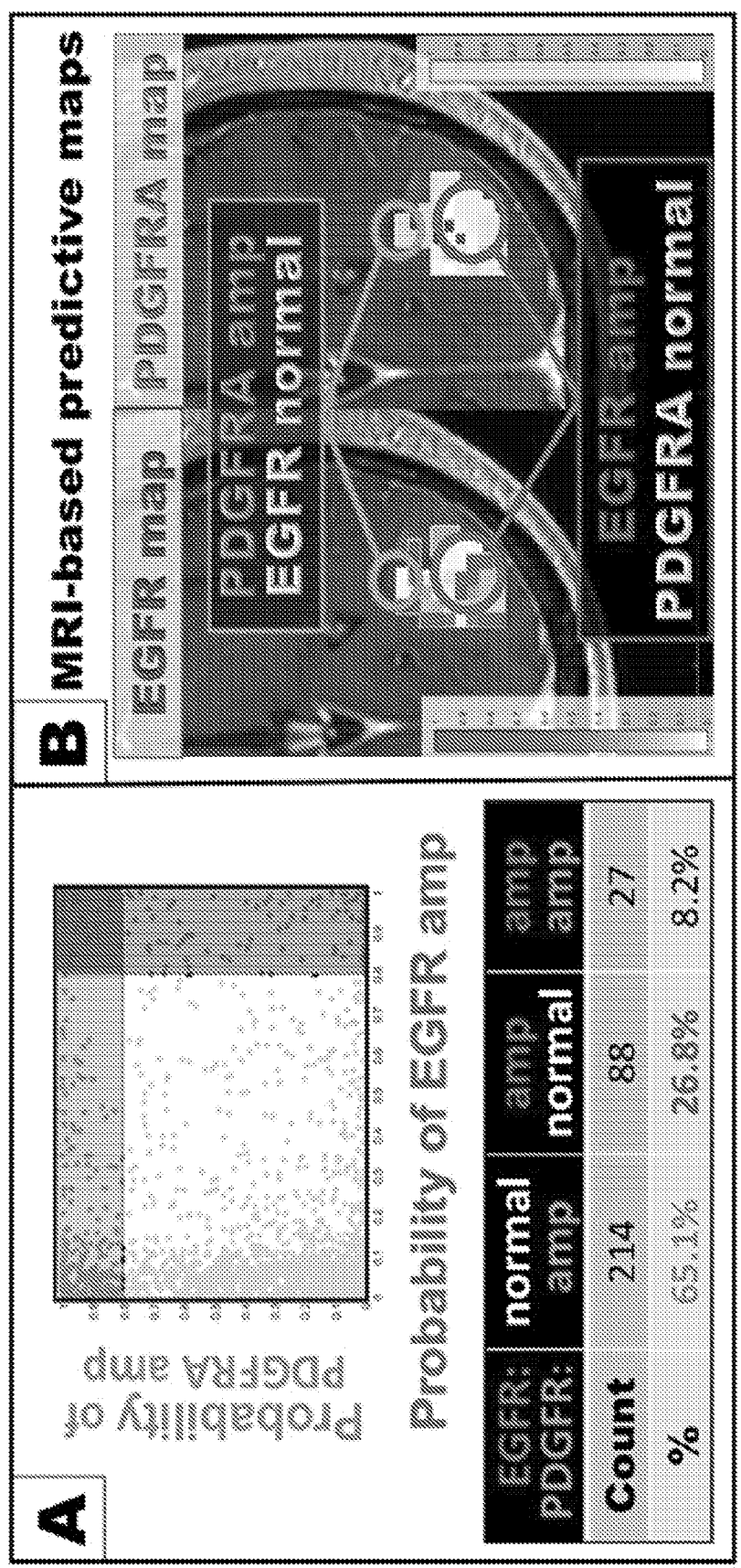
FIGS. 4A and 4B show an example of spatial anti-correlation between model-predicted EGFR amplified (amp) and PDGFR amp subpopulations.

FIGS. 4A and 4B show an example of spatial anti-correlation between model-predicted EGFR amplified (amp) and PDGFR amp subpopulations. FIG. 4A is a scatter plot of model-predicted probability of EGFR amp (x-axis) versus PDGFRA amp (y-axis) for all tumor voxels across 13 GBM patients. The shaded boxes show >80% probability of either EGFR amp (vertically oriented box, shaded red) or PDGFRA amp (horizontally oriented box, shaded green). Only 8.2% of the regions in this example were predicted to contain both amplifications (where the two shaded boxes overlap) (Fisher's exact, p=0.0037). FIG. 4B shows separate ML-generated molecular marker maps for EGFR amp (left) and PDGFRA amp (right) overlaid on the same MRI image slice with probability color bars (0-1) showing colored regions as the highest probability of amplification. The green (upper) circles demarcate an anterior regional subpopulation with PDGFRA amp but normal EGFR, while the red (lower) circles show a posterior subpopulation with EGFR amp but normal PDGFRA. These data illustrate how MRI-based predictive maps can be used to co-localize neighboring molecularly-distinct subpopulations to infer cooperative or competitive dynamics.

Figure 5:
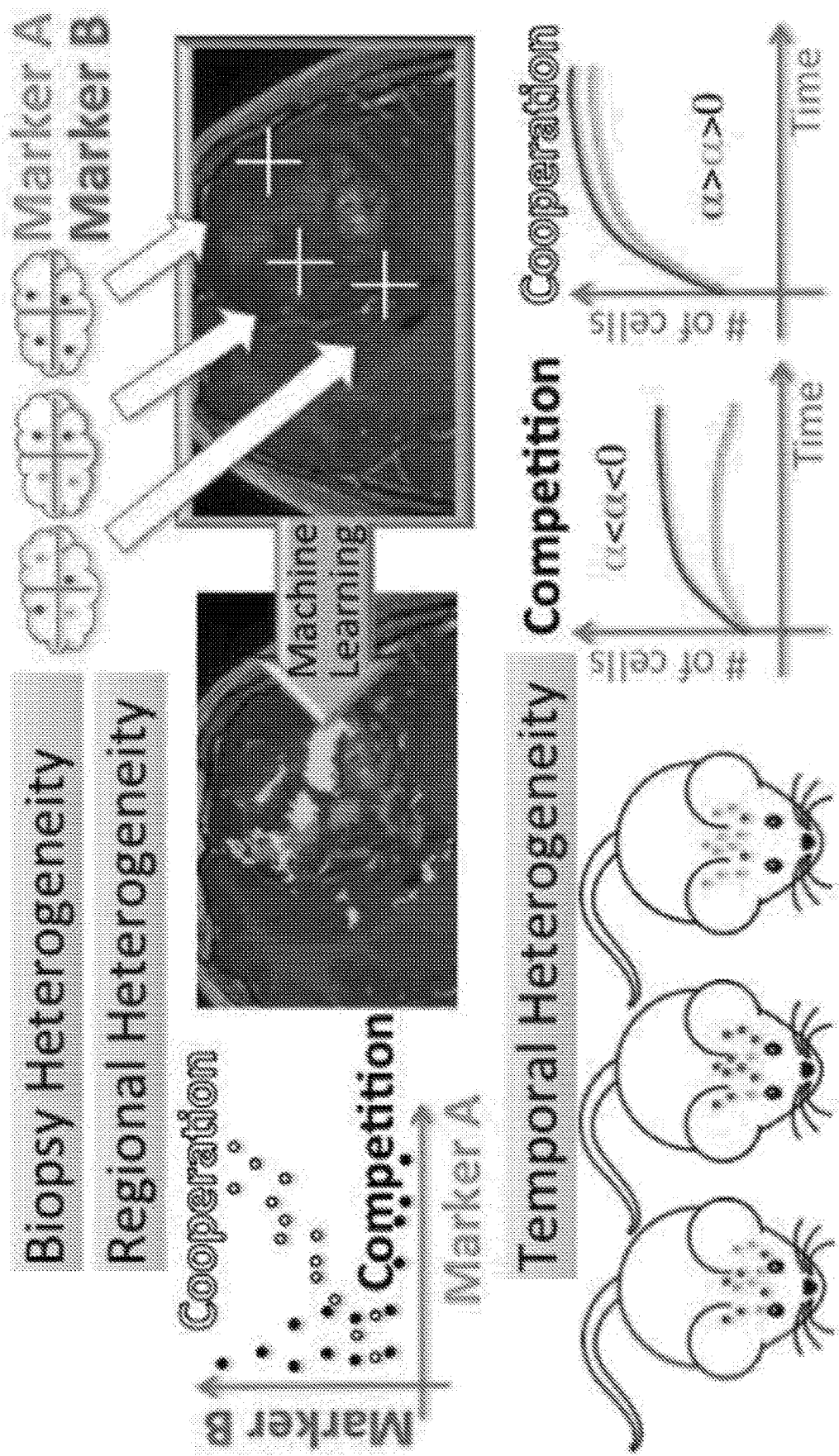
FIG. 5 shows an example outline of a methodology for addressing multi-scale spatial heterogeneity and temporal dynamics using the systems and methods described in the present disclosure.

FIG. 5 shows an example outline of a methodology for addressing multi-scale spatial heterogeneity and temporal dynamics using the systems and methods described in the present disclosure. As described above, image-recorded stereotactic biopsies can be collected and based on these the intra-biopsy heterogeneity of molecular markers of interest can be quantified. These biopsies can be integrated with spatially matched MRI signatures to inform machine learning models that predict spatial patterns of molecular markers across all subregions for the entire tumor. Potential cooperation and competition dynamics can also be identified from co-incidence analysis using biopsies and ML-based molecular marker maps. As noted above, predicted temporal dynamics of cooperation and competition can be quantified and validated in PDX model cell lines expressing appropriate molecular markers of interest. In this way, the clinical relevance of these model-predicted dynamics between molecularly-distinct subpopulations using ML models and serial MRI in human GBM can be further validated.

Figure 6:
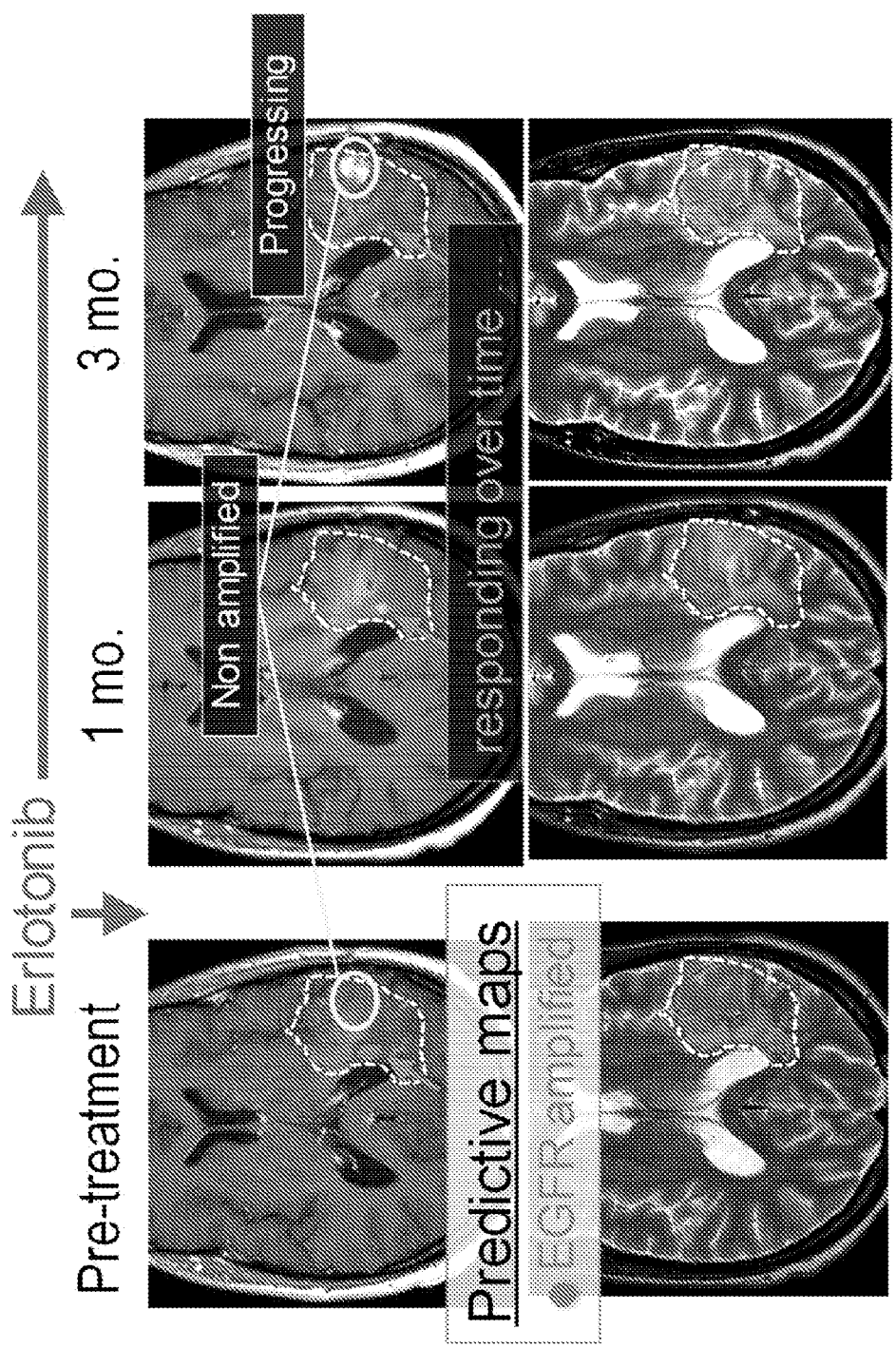
FIG. 6 is an example showing regional differences in response to EGFR inhibition therapy. These results correlate with predictive maps of whether a tumor region is EGFR amplified (i.e., sensitive to EGFR inhibitor therapy) or non-amplified (i.e., insensitive to therapy.

FIG. 6 shows an example of regional differences in response to EGFR inhibition therapy. These results correlate with predictive maps of whether a tumor region is EGFR amplified (i.e., sensitive to EGFR inhibitor therapy) or non-amplified (i.e., insensitive to therapy. In this way, the biomarker maps generated using the systems and methods described in the present disclosure can also provide information about the efficacy or other evaluative information of a particular treatment.

Although the systems and methods have been described with respect to quantifying the regional diversity of molecular markers in a tissue region (e.g., tumor, BAT), it will be appreciated by those skilled in the art that the systems and methods can also be adapted for more general use in any spatially resolved system in which image localized data are available or otherwise possible. For instance, the machine learning models can be constructed based on training data that include spatially sampled data for which a corresponding 2D or 3D image exists, such that the spatially sampled data can be associated with locations within the image. As a non-limiting example, the image could be a satellite image of a geographic region and the spatially sample data may include a local readout of a system or population for which it is desired to model the dynamics over space and time, potentially as interacting with other similarly defined populations or systems.

As one example, the systems and methods described in the present disclosure could be adapted for use in quantifying regional diversity, or otherwise modeling the dynamics of, health data, epidemiological data, or other spatially resolved data over a spatial region, which in some non-limiting examples may be a geographical region. In these instances, machine learning models would be trained on training data that include spatial data or geographic data (e.g., satellite images, census data) rather than MRI data and associated spatially resolved data rather than molecular data collected from spatially annotated biopsy specimens.

For instance, the MRI data described above could be replaced with other types of spatial data, and the molecular data could be replaced with localized data that is distributed and associated with a spatial region. Therefore, like the molecular data collected from spatially annotated biopsy specimens can be correlated with multiparametric MRI data, so can more general spatially localized data be correlated with spatial data. In this way, machine learning models can be trained to generate maps that quantify the regional diversity of spatially localized data across a spatial region, which in some non-limiting examples may be a geographical region. These maps can, in turn, be used to model or otherwise evaluate the spatial and/or temporal dynamics of the localized data within that spatial or geographical region.

As one example, the localized data can include health record data for patients living in a certain geographical region. The health record data can be associated, or otherwise spatially localized, with locations in the geographical region.

As another example, the localized data can include epidemiological data for a certain geographical region. The epidemiological data are associated, or otherwise spatially localized, with locations in the geographical region. For instance, the epidemiological data may include local readouts or other data about the abundance of one or more particular disease epidemics in a geographical region.

As another example, the localized data can include histological data for a certain organ region. The histological data are associated, or otherwise spatially localized, with locations in the organ region. For instance, the histological data may include quantification about the abundance of cells or cell markers in an organ region.

As still another example, the localized data can include demographic data (e.g., gender, age, ethnicity, socioeconomic data), ecological data, geological data, geophysical data, or other spatially resolved data that may be associated with a certain geographical region.

The geographical data can generally include data that defines or depicts geographical regions. For instance, the geographical data may include satellite images of the geographical region. As another example, the geographical data may include census data that defines geographical regions (e.g., census tracts, census block groups, census blocks).

Figure 7:
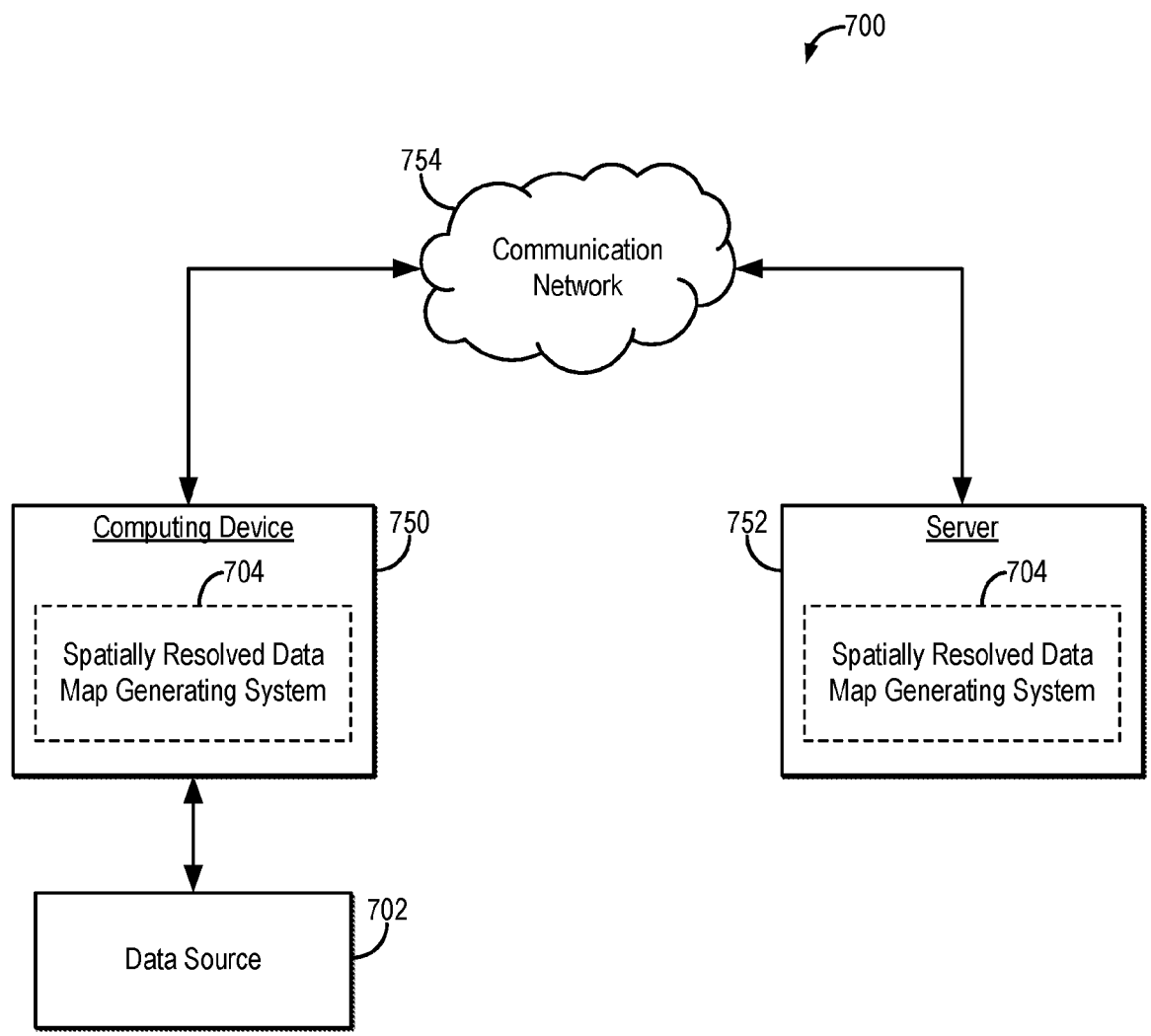
FIG. 7 is a block diagram of an example molecular marker map generating system that can be implemented to construct and implement trained machine learning models that are trained to generate maps depicting spatial patterns of molecular markers and to quantify regional molecularly distinct subpopulations of tumors and/or regions around tumors.

Referring now to FIG. 7, an example of a system 700 for generating maps that quantifying regional diversity of spatially resolved data in one or more regions, in accordance with some embodiments of the systems and methods described in the present disclosure is shown. As shown in FIG. 7, a computing device 750 can receive one or more types of data (e.g., MRI data or other imaging data, molecular data, histology data, biological factor data, geographic data, localized data, spatially resolved data) from data source 702, which may be an MRI data source, a molecular data source, a histology data source, a biological factor data source, a localized data source, a spatially resolved data source, or combinations thereof. In some embodiments, computing device 750 can execute at least a portion of a spatially resolved data map generating system 704 to construct and implement machine learning models that are able to generate maps that depict spatial patterns in spatially resolved data (e.g., molecular markers, biomarkers) from data received from the data source 702.

Additionally or alternatively, in some embodiments, the computing device 750 can communicate information about data received from the data source 702 to a server 752 over a communication network 754, which can execute at least a portion of the spatially resolved data map generating system 704 to construct and implement machine learning models that are able to generate maps that depict spatial patterns in spatially resolved data (e.g., molecular markers, biomarkers) from data received from the data source 702. In such embodiments, the server 752 can return information to the computing device 750 (and/or any other suitable computing device) indicative of an output of the spatially resolved data map generating system 704.

In some embodiments, computing device 750 and/or server 752 can be any suitable computing device or combination of devices, such as a desktop computer, a laptop computer, a smartphone, a tablet computer, a wearable computer, a server computer, a virtual machine being executed by a physical computing device, and so on. The computing device 750 and/or server 752 can also reconstruct images from the data.

In some embodiments, data source 702 can be any suitable source of imaging data (e.g., measurement data, images reconstructed from measurement data), such as an MRI system or other medical or optical imaging system, another computing device (e.g., a server storing image data), and so on. In some embodiments, data source 702 can be local to computing device 750. For example, data source 702 can be incorporated with computing device 750 (e.g., computing device 750 can be configured as part of a device for capturing, scanning, and/or storing images). As another example, data source 702 can be connected to computing device 750 by a cable, a direct wireless link, and so on. Additionally or alternatively, in some embodiments, data source 702 can be located locally and/or remotely from computing device 750, and can communicate data to computing device 750 (and/or server 752) via a communication network (e.g., communication network 754).

In some embodiments, communication network 754 can be any suitable communication network or combination of communication networks. For example, communication network 754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Figure 8:
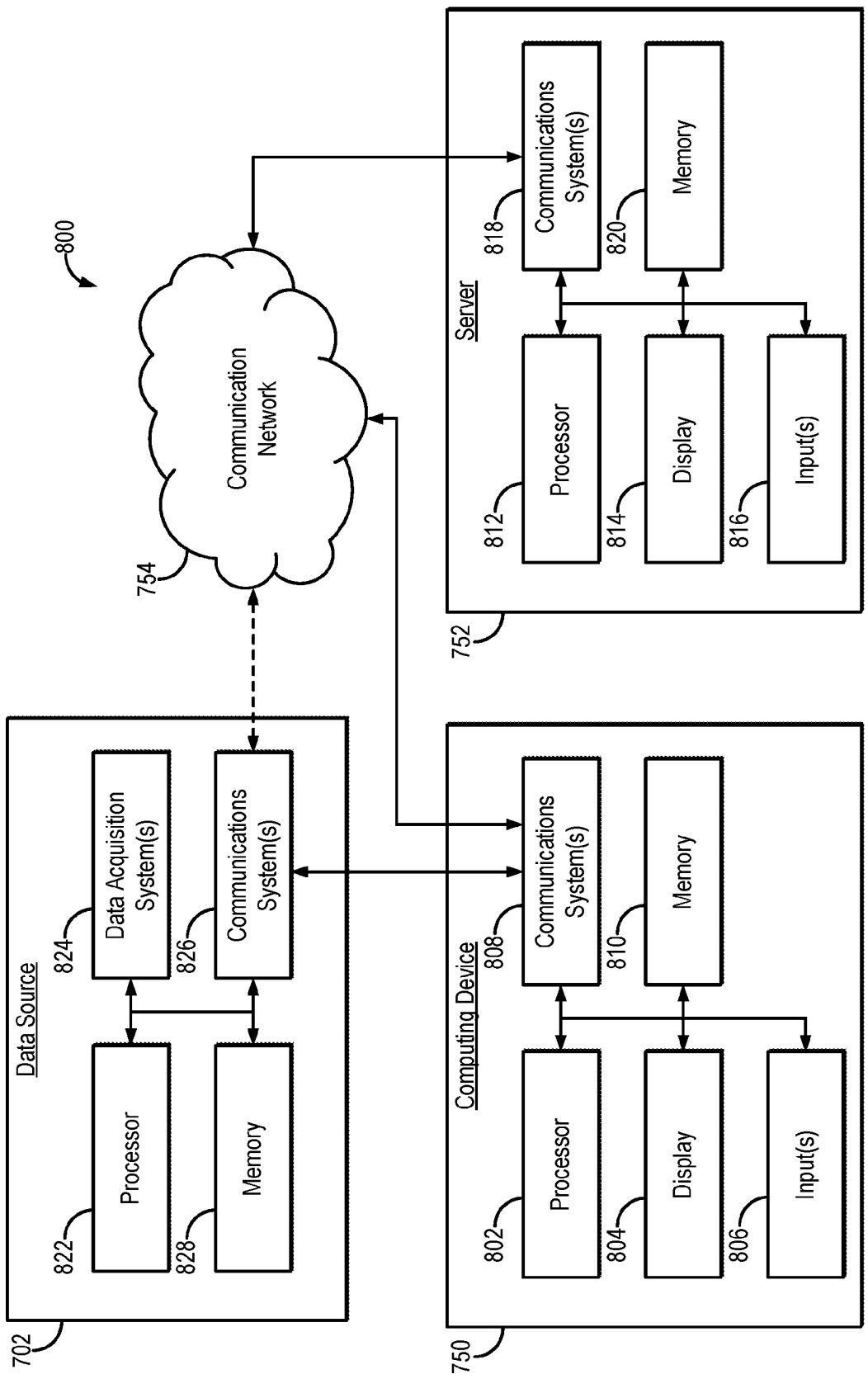
FIG. 8 is a block diagram showing examples of hardware components that can implement the molecular marker map generating system of FIG. 7.

Referring now to FIG. 8, an example of hardware 800 that can be used to implement data source 702, computing device 750, and server 754 in accordance with some embodiments of the systems and methods described in the present disclosure is shown. As shown in FIG. 8, in some embodiments, computing device 750 can include a processor 802, a display 804, one or more inputs 806, one or more communication systems 808, and/or memory 810. In some embodiments, processor 802 can be any suitable hardware processor or combination of processors, such as a central processing unit ("CPU"), a graphics processing unit ("GPU"), and so on. In some embodiments, display 804 can include any suitable display devices, such as a computer monitor, a touchscreen, a television, and so on. In some embodiments, inputs 806 can include any suitable input devices and/or sensors that can be used to receive user input, such as a keyboard, a mouse, a touchscreen, a microphone, and so on.

In some embodiments, communications systems 808 can include any suitable hardware, firmware, and/or software for communicating information over communication network 754 and/or any other suitable communication networks. For example, communications systems 808 can include one or more transceivers, one or more communication chips and/or chip sets, and so on. In a more particular example, communications systems 808 can include hardware, firmware and/or software that can be used to establish a Wi-Fi connection, a Bluetooth connection, a cellular connection, an Ethernet connection, and so on.

In some embodiments, memory 810 can include any suitable storage device or devices that can be used to store instructions, values, data, or the like, that can be used, for example, by processor 802 to present content using display 804, to communicate with server 752 via communications system(s) 808, and so on. Memory 810 can include any suitable volatile memory, non-volatile memory, storage, or any suitable combination thereof. For example, memory 810 can include RAM, ROM, EEPROM, one or more flash drives, one or more hard disks, one or more solid state drives, one or more optical drives, and so on. In some embodiments, memory 810 can have encoded thereon, or otherwise stored therein, a computer program for controlling operation of computing device 750. In such embodiments, processor 802 can execute at least a portion of the computer program to present content (e.g., images, user interfaces, graphics, tables), receive content from server 752, transmit information to server 752, and so on.

In some embodiments, server 752 can include a processor 812, a display 814, one or more inputs 816, one or more communications systems 818, and/or memory 820. In some embodiments, processor 812 can be any suitable hardware processor or combination of processors, such as a CPU, a GPU, and so on. In some embodiments, display 814 can include any suitable display devices, such as a computer monitor, a touchscreen, a television, and so on. In some embodiments, inputs 816 can include any suitable input devices and/or sensors that can be used to receive user input, such as a keyboard, a mouse, a touchscreen, a microphone, and so on.

In some embodiments, communications systems 818 can include any suitable hardware, firmware, and/or software for communicating information over communication network 754 and/or any other suitable communication networks. For example, communications systems 818 can include one or more transceivers, one or more communication chips and/or chip sets, and so on. In a more particular example, communications systems 818 can include hardware, firmware and/or software that can be used to establish a Wi-Fi connection, a Bluetooth connection, a cellular connection, an Ethernet connection, and so on.

In some embodiments, memory 820 can include any suitable storage device or devices that can be used to store instructions, values, data, or the like, that can be used, for example, by processor 812 to present content using display 814, to communicate with one or more computing devices 750, and so on. Memory 820 can include any suitable volatile memory, non-volatile memory, storage, or any suitable combination thereof. For example, memory 820 can include RAM, ROM, EEPROM, one or more flash drives, one or more hard disks, one or more solid state drives, one or more optical drives, and so on. In some embodiments, memory 820 can have encoded thereon a server program for controlling operation of server 752. In such embodiments, processor 812 can execute at least a portion of the server program to transmit information and/or content (e.g., data, images, a user interface) to one or more computing devices 750, receive information and/or content from one or more computing devices 750, receive instructions from one or more devices (e.g., a personal computer, a laptop computer, a tablet computer, a smartphone), and so on.

In some embodiments, data source 702 can include a processor 822, one or more data acquisition systems 824, one or more communications systems 826, and/or memory 828. In some embodiments, processor 822 can be any suitable hardware processor or combination of processors, such as a CPU, a GPU, and so on. In some embodiments, the one or more data acquisition systems 824 are generally configured to acquire data, images, or both, and can include an MRI system. Additionally or alternatively, in some embodiments, one or more data acquisition systems 824 can include any suitable hardware, firmware, and/or software for coupling to and/or controlling operations of an MRI system. In some embodiments, one or more portions of the one or more data acquisition systems 824 can be removable and/or replaceable.

Note that, although not shown, data source 702 can include any suitable inputs and/or outputs. For example, data source 702 can include input devices and/or sensors that can be used to receive user input, such as a keyboard, a mouse, a touchscreen, a microphone, a trackpad, a trackball, and so on. As another example, data source 702 can include any suitable display devices, such as a computer monitor, a touchscreen, a television, etc., one or more speakers, and so on.

In some embodiments, communications systems 826 can include any suitable hardware, firmware, and/or software for communicating information to computing device 750 (and, in some embodiments, over communication network 754 and/or any other suitable communication networks). For example, communications systems 826 can include one or more transceivers, one or more communication chips and/or chip sets, and so on. In a more particular example, communications systems 826 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 828 can include any suitable storage device or devices that can be used to store instructions, values, data, or the like, that can be used, for example, by processor 822 to control the one or more data acquisition systems 824, and/or receive data from the one or more data acquisition systems 824; to images from data; present content (e.g., images, a user interface) using a display; communicate with one or more computing devices 750; and so on. Memory 828 can include any suitable volatile memory, non-volatile memory, storage, or any suitable combination thereof. For example, memory 828 can include RAM, ROM, EEPROM, one or more flash drives, one or more hard disks, one or more solid state drives, one or more optical drives, and so on. In some embodiments, memory 828 can have encoded thereon, or otherwise stored therein, a program for controlling operation of data source 702. In such embodiments, processor 822 can execute at least a portion of the program to generate images, transmit information and/or content (e.g., data, images) to one or more computing devices 750, receive information and/or content from one or more computing devices 750, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 9:
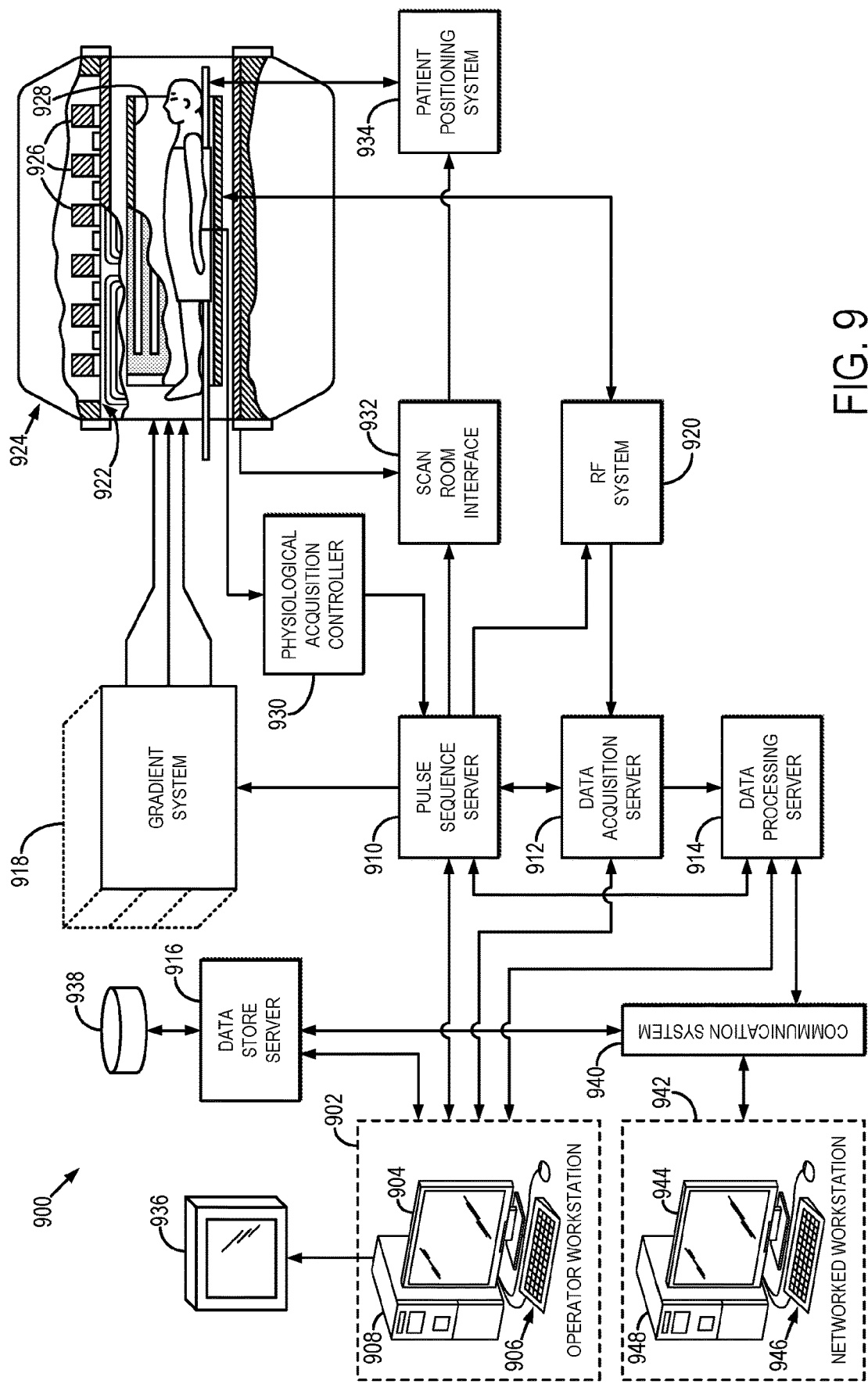
FIG. 9 is a block diagram of an example MRI system that can be implemented to acquire MRI data.

Referring particularly now to FIG. 9, an example of an MRI system 900 that can implement the methods described here is illustrated. The MRI system 900 includes an operator workstation 902 that may include a display 904, one or more input devices 906 (e.g., a keyboard, a mouse), and a processor 908. The processor 908 may include a commercially available programmable machine running a commercially available operating system. The operator workstation 902 provides an operator interface that facilitates entering scan parameters into the MRI system 900. The operator workstation 902 may be coupled to different servers, including, for example, a pulse sequence server 910, a data acquisition server 912, a data processing server 914, and a data store server 916. The operator workstation 902 and the servers 910, 912, 914, and 916 may be connected via a communication system 940, which may include wired or wireless network connections.

The pulse sequence server 910 functions in response to instructions provided by the operator workstation 902 to operate a gradient system 918 and a radiofrequency ("RF") system 920. Gradient waveforms for performing a prescribed scan are produced and applied to the gradient system 918, which then excites gradient coils in an assembly 922 to produce the magnetic field gradients $G_x$, $G_y$, and $G_z$ that are used for spatially encoding magnetic resonance signals. The gradient coil assembly 922 forms part of a magnet assembly 924 that includes a polarizing magnet 926 and a whole-body RF coil 928.

RF waveforms are applied by the RF system 920 to the RF coil 928, or a separate local coil to perform the prescribed magnetic resonance pulse sequence. Responsive magnetic resonance signals detected by the RF coil 928, or a separate local coil, are received by the RF system 920. The responsive magnetic resonance signals may be amplified, demodulated, filtered, and digitized under direction of commands produced by the pulse sequence server 910. The RF system 920 includes an RF transmitter for producing a wide variety of RF pulses used in MRI pulse sequences. The RF transmitter is responsive to the prescribed scan and direction from the pulse sequence server 910 to produce RF pulses of the desired frequency, phase, and pulse amplitude waveform. The generated RF pulses may be applied to the whole-body RF coil 928 or to one or more local coils or coil arrays.

The RF system 920 also includes one or more RF receiver channels. An RF receiver channel includes an RF preamplifier that amplifies the magnetic resonance signal received by the coil 928 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (3);$$

and the phase of the received magnetic resonance signal may also be determined according to the following relationship:

$$\varphi = \tan^{-1}\left(\frac{Q}{I}\right). \quad (4)$$

The pulse sequence server 910 may receive patient data from a physiological acquisition controller 930. By way of example, the physiological acquisition controller 930 may receive signals from a number of different sensors connected to the patient, including electrocardiograph ("ECG") signals from electrodes, or respiratory signals from a respiratory bellows or other respiratory monitoring devices. These signals may be used by the pulse sequence server 910 to synchronize, or "gate," the performance of the scan with the subject's heart beat or respiration.

The pulse sequence server 910 may also connect to a scan room interface circuit 932 that receives signals from various sensors associated with the condition of the patient and the magnet system. Through the scan room interface circuit 932, a patient positioning system 934 can receive commands to move the patient to desired positions during the scan.

The digitized magnetic resonance signal samples produced by the RF system 920 are received by the data acquisition server 912. The data acquisition server 912 operates in response to instructions downloaded from the operator workstation 902 to receive the real-time magnetic resonance data and provide buffer storage, so that data is not lost by data overrun. In some scans, the data acquisition server 912 passes the acquired magnetic resonance data to the data processor server 914. In scans that require information derived from acquired magnetic resonance data to control the further performance of the scan, the data acquisition server 912 may be programmed to produce such information and convey it to the pulse sequence server 910. For example, during pre-scans, magnetic resonance data may be acquired and used to calibrate the pulse sequence performed by the pulse sequence server 910. As another example, navigator signals may be acquired and used to adjust the operating parameters of the RF system 920 or the gradient system 918, or to control the view order in which k-space is sampled. In still another example, the data acquisition server 912 may also process magnetic resonance signals used to detect the arrival of a contrast agent in a magnetic resonance angiography ("MRA") scan. For example, the data acquisition server 912 may acquire magnetic resonance data and processes it in real-time to produce information that is used to control the scan.

The data processing server 914 receives magnetic resonance data from the data acquisition server 912 and processes the magnetic resonance data in accordance with instructions provided by the operator workstation 902. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 914 are conveyed back to the operator workstation 902 for storage. Real-time images may be stored in a data base memory cache, from which they may be output to operator display 902 or a display 936. Batch mode images or selected real time images may be stored in a host database on disc storage 938. When such images have been reconstructed and transferred to storage, the data processing server 914 may notify the data store server 916 on the operator workstation 902. The operator workstation 902 may be used by an operator to archive the images, produce films, or send the images via a network to other facilities.

The MRI system 900 may also include one or more networked workstations 942. For example, a networked workstation 942 may include a display 944, one or more input devices 946 (e.g., a keyboard, a mouse), and a processor 948. The networked workstation 942 may be located within the same facility as the operator workstation 902, or in a different facility, such as a different healthcare institution or clinic.

The networked workstation 942 may gain remote access to the data processing server 914 or data store server 916 via the communication system 940. Accordingly, multiple networked workstations 942 may have access to the data processing server 914 and the data store server 916. In this manner, magnetic resonance data, reconstructed images, or other data may be exchanged between the data processing server 914 or the data store server 916 and the networked workstations 942, such that the data or images may be remotely processed by a networked workstation 942.

The present disclosure has described one or more preferred embodiments, and it should be appreciated that many equivalents, alternatives, variations, and modifications, aside from those expressly stated, are possible and within the scope of the invention.

The invention claimed is:

1. A method for constructing and implementing a machine learning model to generate at least one image that depicts spatial patterns of a molecular marker across a region-of-interest in a subject, the steps of the method comprising:
   constructing a trained machine learning model by:
   (i) accessing training data with a computer system, the training data comprising magnetic resonance imaging (MRI) data acquired from one or more subjects and molecular data determined from biopsies collected from the one or more subjects, wherein the molecular data comprises DNA copy number variation (CNV) data and exome data;
   (ii) quantifying regional molecular diversity in the one or more subjects from the molecular data;
   (iii) training a machine learning model based on the training data and the quantified regional molecular diversity in the one or more subjects, wherein the machine learning model is trained on the training data to localize molecularly distinct subpopulations and phenotypic niches across a region-of-interest; and
   generating an image that depicts spatial patterns of a molecular marker across a region-of-interest in a subject by inputting magnetic resonance images acquired from the subject to the trained machine learning model.

2. The method as recited in claim 1, wherein the region-of-interest includes a brain around tumor (BAT) region.

3. The method as recited in claim 1, wherein the training data further comprises biological factor data including at least one of a sex or an age of each of the one or more subjects.

4. The method as recited in claim 3, wherein the biological factor data includes the sex of each of the one or more subjects and step (iii) includes training a first machine learning model based the training data and the quantified regional molecular diversity in the one or more subjects associated with a female sex and training a second machine learning model based the training data and the quantified regional molecular diversity in the one or more subjects associated with a male sex.

5. The method as recited in claim 4, wherein the image whose pixel values quantify regional molecular diversity in the region-of-interest in the subject is generated by inputting magnetic resonance images acquired from the subject to the first machine learning model when the subject is a female and to the second machine learning model when the subject is a male.

6. The method as recited in claim 1, wherein the molecular data corresponds to a plurality of different molecular markers and step (iii) includes training a different machine learning model for each of the plurality of different molecular markers based on the training data and the quantified regional molecular diversity in the plurality of subjects associated with each different molecular marker.

7. The method as recited in claim 6, wherein the molecular marker includes at least one of EGFR, PDGFRA, PTEN, NF1, TP53, CDKN2A, RB1, ATRX, or MET.

8. The method as recited in claim 1, wherein quantifying regional molecular diversity in the plurality of subjects from the molecular data includes quantifying intra-biopsy heterogeneity.

9. The method as recited in claim 8, wherein intra-biopsy heterogeneity is quantified based on a presence of a molecular marker throughout biopsy sub-regions, an absence of a molecular marker throughout biopsy sub-regions, or an admixture of a molecular marker being present and absent throughout biopsy sub-regions.

10. The method as recited in claim 1, wherein quantifying regional molecular diversity in the one or more subjects from the molecular data includes quantifying correlations between different molecular markers.

11. The method as recited in claim 1, wherein the molecular data further comprises at least one of RNA sequencing (RNA-seq), gene expression, proteomics analysis data, or combinations thereof.

12. The method as recited in claim 11, wherein quantifying regional molecular diversity in the one or more subjects from the molecular data includes classifying molecularly distinct subpopulations based on at least one of the CNV data and the exome data.

13. The method as recited in claim 11, wherein the molecular marker is a phenotypic marker and quantifying regional molecular diversity in the one or more subjects from the molecular data includes quantifying phenotypic niches based on RNA-seq.

14. The method as recited in claim 13, wherein the phenotypic marker indicates at least one of hypoxia, cell proliferation, angiogenesis, cell invasion, or combinations thereof.

15. The method as recited in claim 1, wherein the MRI data comprises magnetic resonance images and parametric maps generated from the magnetic resonance images.

16. The method as recited in claim 15, wherein the magnetic resonance images include at least one of T1-weighted images, post-contrast T1-weighted images, T2-weighted images, post-contrast T2-weighted images, T2*-weighted images, post-contrast T2*- weighted images, diffusion-weighted images, perfusion-weighted images, or combinations thereof.

17. The method as recited in claim 15, wherein the parametric maps include at least one of relative cerebral blood volume, mean diffusivity, fractional anisotropy, or combinations thereof.

18. The method as recited in claim 15, wherein the MRI data further comprises texture feature maps generated from at least one of the magnetic resonance images or the parametric maps.

19. The method as recited in claim 18, wherein the texture feature maps include texture features computed based on at least one of a gray-level co-occurrence matrix (GLCM), local binary patterns (LBP), a discrete orthonormal Stockwell transform (DOST), or a Gabor filter.

20. The method as recited in claim 1, wherein the trained machine learning model is a transfer learning model trained on MRI data and molecular data acquired from the subject.

21. The method as recited in claim 1, wherein quantifying regional molecular diversity in the one or more subjects from the molecular data comprises quantifying the molecular diversity based on one or more continuous variables.

* * * * *